United States Patent
Mairal et al.

(10) Patent No.: US 6,846,909 B2
(45) Date of Patent: Jan. 25, 2005

(54) ZEIN RECOVERY USING NON-POROUS MEMBRANES

(75) Inventors: Anurag P. Mairal, Fremont, CA (US); Alvin Ng, Palo Alto, CA (US); Johannes G. Wijmans, Menlo Park, CA (US)

(73) Assignee: Membrane Technology and Research, Inc., Menlo Park, CA (US)

(*) Notice: Subject to any disclaimer, the term of this patent is extended or adjusted under 35 U.S.C. 154(b) by 0 days.

(21) Appl. No.: 10/437,589

(22) Filed: May 14, 2003

(65) Prior Publication Data

US 2004/0230041 A1 Nov. 18, 2004

(51) Int. Cl.$^7$ ............................................. C07K 14/415
(52) U.S. Cl. ........................................................ 530/373
(58) Field of Search ........................................ 530/373

(56) References Cited

U.S. PATENT DOCUMENTS

| | | |
|---|---|---|
| 4,624,805 A | 11/1986 | Lawhon |
| 4,963,165 A | 10/1990 | Blume et al. |
| 5,145,584 A | 9/1992 | Swamikannu |
| 5,410,021 A | 4/1995 | Kampen |
| 6,433,146 B1 * | 8/2002 | Cheryan ................. 530/373 |
| 2002/0183490 A1 | 12/2002 | Cheryan |

OTHER PUBLICATIONS

N. Singh et al., "Membrane Technology in Corn Wet Milling," Cereal Foods World, Jul. 1997, vol. 42, No. 7, p. 520–525.

K. Ebert et al., "Solvent resistant nanofiltration membranes in edible oil processing," Membrane Technology, 1999, No. 107, p. 5–8.

S. Nunes et al., "Dense hydrophilic composite membranes for ultrafiltration." Journal of Membrane Science, 1995, vol. 106, p. 49–56.

* cited by examiner

Primary Examiner—Karen Cochrane Carlson
Assistant Examiner—Anand U Desai
(74) Attorney, Agent, or Firm—J. Farrant

(57) ABSTRACT

A membrane process for treating zein solutions to increase the zein concentration in the solution. The process uses a non-porous membrane that preferentially permeates the solvent and rejects the zein. Optionally, the process can be operated as a diafiltration process to yield a concentrate of high zein purity.

57 Claims, 27 Drawing Sheets

ZEIN RECOVERY USING NON-POROUS MEMBRANES

This invention was made in part with Government support under award numbers DE-FG03-98ER82617 and DE-FG36-02GO12057, both awarded by the Department of Energy. The Government has certain rights in this invention.

FIELD OF THE INVENTION

The invention relates to the treatment of zein solutions by means of dense, non-porous filtration membranes.

BACKGROUND OF THE INVENTION

Zein, a mixture of water-insoluble proteins, is a valuable by-product of corn processing. To extract and purify zein requires a complicated train of steps, so costs are high, and zein in purified form currently sells for up to $10/lb or more. As a result, uses of purified zein are limited to specialty applications that can tolerate this price, such as pharmaceutical tablet coatings or confectionery coatings. Most zein remains unextracted and is simply carried over into comparatively low-value products, such as animal feed.

However, zein has many potential uses, including edible coatings for foodstuffs and biodegradable polymer resins, and a broader market for zein would improve the overall economics of corn processing.

U.S. Pat. No. 4,624,805, to Texas A&M University, describes a process for recovery of protein from a corn slurry, including an ultrafiltration step using Romicon PM30 membranes or the like.

U.S. Pat. No. 5,410,021, to Energenetics, Inc., describes recovery of various protein fractions from corn, including an ultrafiltration step using inorganic microfiltration membranes, such as aluminum oxide membranes.

U.S. Pat. No. 6,433,146 and U.S. Patent Application Publication 2002/0183490, both to the University of Illinois, describe an integrated process that can be optimized to maximize production of oil or zein. The process includes ultrafiltration, nanofiltration and pervaporation steps.

An article by N. Singh et al., entitled "Membrane Technology in Corn Wet Milling," (*Cereal Foods World*, Vol. 42, No. 7, pp. 520–525, July 1997), includes a section describing techniques for protein recovery from corn gluten meal, including microfiltration and ultrafiltration steps.

Most ultrafiltration membranes, including those mentioned in the references cited above, are porous, and are subject to internal fouling by components of the feed solution. Internal fouling is usually irreversible and may cause the transmembrane flux to decline to an unacceptable level in a matter of weeks or months. At this point, the only solution is to replace the membranes.

A few attempts to use non-porous membranes as ultrafiltration membranes have been reported in the literature.

U.S. Pat. No. 5,145,584, to Allied Signal, Inc., describes use of a composite ultrafiltration membrane having a dense coating of a polyelectrolyte complex for separating glucose from higher molecular weight sugars.

An article by K. Ebert et al., "Solvent resistant nanofiltration membranes in edible oil processing," (*Membrane Technology*, No. 107, p. 5–8, 1999), describes the use of composite membranes having a non-porous cellulose or polyether-polyamide block copolymer selective coating layer in experiments relating to separation of rapeseed oil from acetone. The reference also cites fluxes for pure 2-propanol and ethanol through both membrane types.

An article by S. Nunes et al., "Dense hydrophilic composite membranes for ultrafiltration," (*J. Membrane Science*, Vol. 106, p. 49–56, 1995), compares the fouling resistance of composite membranes having a polyether-polyamide block copolymer selective coating layer with that of various commercial membranes. The membranes have molecular weight cut-offs between about 800 and 4,500. The experimental membranes showed fouling resistance as good or better than commercial membranes when tested with oil-in-water emulsions or with milk containing 3.5 wt % fat.

German Patent DE4237604, to GKSS, includes similar experimental details to those of the Nunes et al. paper. The patent covers the uses of a non-porous membrane made from a polymer having a polyether segment in the ultrafiltration treatment of aqueous solutions.

It is an object of the invention to provide a membrane filtration process for separation of zein from a solvent.

Additional objects and advantages of the invention will be apparent from the description below to those of ordinary skill in the art.

SUMMARY OF THE INVENTION

The invention is a process for treating solutions of zein in a solvent, particularly a non-aqueous-based solvent, to increase the zein concentration, and preferably to increase the zein purity.

The invention involves running the zein solution across the feed side of a membrane that preferentially permeates the solvent and rejects the zein.

The invention in its most basic embodiment comprises the following steps:
(a) providing a composite membrane having a feed side, a permeate side, and a dense, non-porous selective layer that is selective in favor of a solvent over zein;
(b) passing a feed solution comprising zein and the solvent across the feed side of the membrane;
(c) withdrawing from the feed side a residue stream enriched in zein compared to the feed solution;
(d) withdrawing from the permeate side a permeate stream depleted in zein compared to the feed solution.

Thus, the process results in a zein-enriched retentate stream and a zein-depleted permeate solvent stream.

Generally, the zein content of the feed solution is less than about 5 wt %, and typically it is no more than about 2 wt %. The feed solution usually contains a number of other solute components in addition to zein, such as starches, sugars, fatty acids, alcohols and protein fragments. The zein weight fraction of the total solute components is usually less than 100%, and may be as low as 50%, 40% or less.

The solvent may be any solvent that dissolves zein. The solvent is usually, but not necessarily, non-aqueous, by which we mean that water is not the major component. Typical solvents include alcohols and alcohol/water mixtures.

The membranes used in the invention preferably take the form of a composite structure, comprising a microporous support membrane overcoated with a dense, non-porous, hydrophilic polymer layer that is primarily responsible for the separation properties.

We have discovered that such dense, composite membranes have properties that render them unexpectedly valuable for treating non-aqueous-based solutions in which zein and sugars are dissolved. When confronted with alcohol-based solutions, for example, the membranes, although essentially non-porous, exhibit a molecular weight cut-off that enables them to retain the bulk of the zein fraction, but permeate the sugars and other smaller solutes and the solvent.

The membranes typically exhibit a zein rejection of at least about 90%, and often higher, such as at least about 95% or even 99% or above. The sugar rejection is typically much lower, such as no more than about 50%, 40%, or lower, such as no more than about 20% or 10%.

Thus, the membranes can not only increase the solids concentration in the solution, but can decrease the non-zein content, that is, increase the zein purity, of the solids that may subsequently be recovered. In other words, the process provides a fractionation, as well as a concentration, capability. High increases in zein purity of the solute, such as from below 30%, 40% or 50% zein in the raw feed to above 70%, 80% or 90% zein in the final residue, are frequently possible with our process.

In the aspect in which the process provides this fractionation capability, the invention comprises the following steps:
(a) providing a first composite membrane having a first feed side, a first permeate side, and a first dense, non-porous selective layer that is selective in favor of the solvent over zein and that exhibits a zein rejection and a sugar rejection, the sugar rejection being lower than the zein rejection;
(b) passing the feed solution across the first feed side;
(c) withdrawing from the first feed side a first residue stream enriched in zein compared to the feed solution;
(d) withdrawing from the first permeate side a first permeate stream having a permeate dissolved solids content that is enriched in sugar and depleted in zein compared to the solute.

In all aspects, the most preferred polymer for the dense, non-porous selective layer is a polyamide-polyether block copolymer, commercially available as Pebax® and described in detail in U.S. Pat. No. 4,963,165.

Since the membrane is non-porous, internal fouling by pore-plugging cannot occur.

The process is usually operated with the feed solution under a modest pressure, so as to limit the formation of a zein gel layer on the surface of the membrane. In general, feed pump operating pressures of below about 150 psig are preferred, although the upper limit of the preferred range decreases as the zein concentration in the feed increases.

The membranes should preferably provide a pressure-normalized solvent flux, averaged over the process operating time, of at least about 0.05 L/m² ·h·psi.

The process may be carried out according to any convenient time table (such as continuously, batchwise according to a regular schedule, or on demand) and in any convenient mode (such as single-pass, partial recirculation, or full recirculation), to integrate it as desired with other operations.

The process may be operated using a single membrane separation stage, or may be carried out using multiple membrane separation steps as desired.

It is sometimes advantageous to operate the process as a diafiltration process, as explained in detail below, to improve the purity of the zein in the retentate.

In addition to containing solvent, the permeate stream from the membrane separation step usually contains solutes that were present in the raw feed solution. The zein rejection of the membranes is high, so the permeate solute fraction is predominantly made up of sugars and other low molecular weight materials. The permeate stream may be subjected to further treatment to separate the solvent from the other components, or sent to any other convenient destination.

Normally, the process provides a substantial reduction in the volume of zein solution, and a several-fold concentration of zein, from feed to retentate. Preferably, the retentate volume at the end of the process is no more than about 30 vol %, 20 vol % or even 10 vol % of the raw feed volume. This degree of concentration corresponds to a solids concentration in the recovered retentate between about five and ten times higher than that of the feed. A typical increase in concentration might be from 1.2 wt % to 7 wt %, for example.

The zein-enriched residue stream from the membrane separation step may optionally be recirculated in whole or part to the membrane separation step for further concentration and/or subjected to any other treatment, such as to render the zein suitable for use in industrial or food applications.

The high levels of concentration, that is, solvent reduction, provided by the process facilitate subsequent steps that may be used to recover the zein in dry form. The energy used for spray drying, for example, may be reduced by as much as an order of magnitude or more.

It is to be understood that the above summary and the following detailed description are intended to explain and illustrate the invention without restricting its scope.

DETAILED DESCRIPTION OF THE INVENTION

Figure 1:
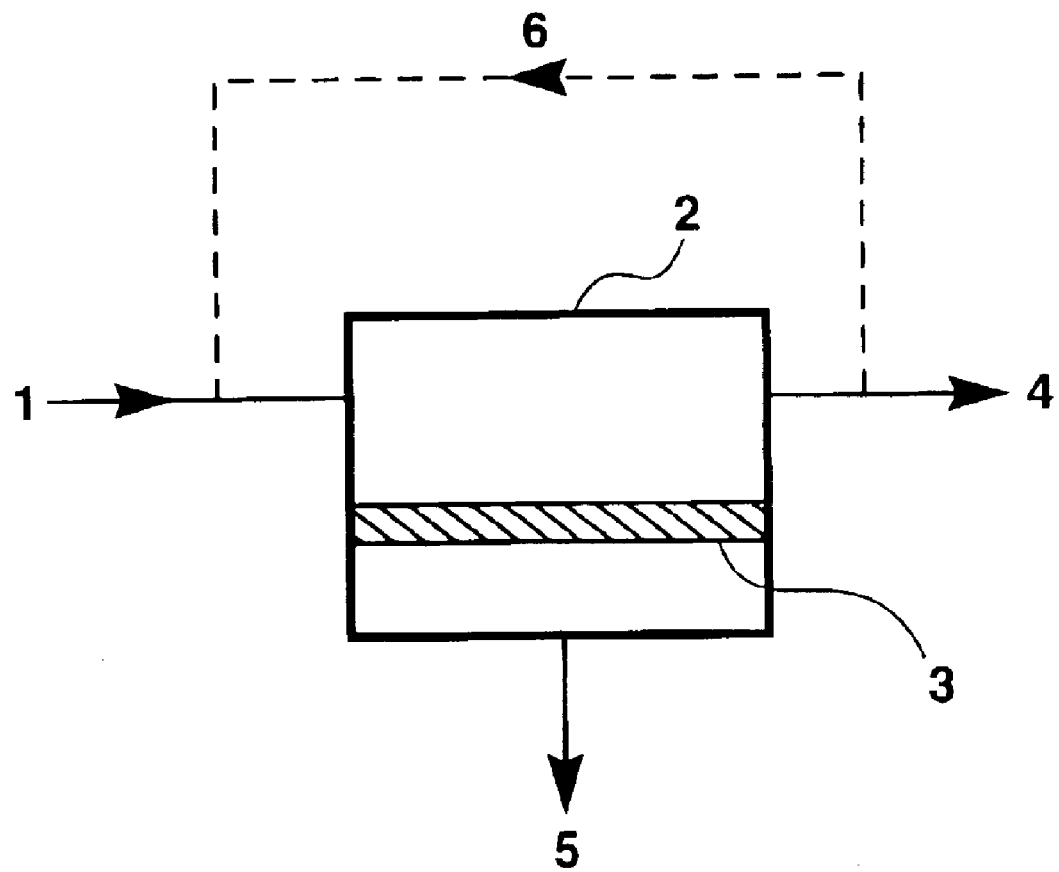
FIG. 1 is a schematic drawing of a basic embodiment of the separation process of the invention.

Percentages cited herein are by volume when referring to liquids and by weight when referring to solids, unless stated otherwise.

Zein is a mixture of water-insoluble proteins that makes up about 5 wt % of corn or maize kernels. Zein proteins are also sometimes referred to as prolamines. These proteins are relatively small, having molecular weights typically between about 12,000 and 40,000 dalton.

The invention is a process for treating solutions of zein, by running the zein solution across the feed side of a membrane that preferentially permeates the solvent and rejects the zein. A non-limiting goal of the invention is to produce amore concentrated zein solution that may subsequently be further processed to provide a purified zein product.

The solution to be treated may arise from any source. Typically, such solutions are generated as a step in corn processing. For example, they may arise when proteins are extracted from corn meal, corn germ, corn gluten meal, or other corn by-products.

In many cases, the solution may have been treated upstream of the present process, such as by other filtration steps, by centrifugation and so on, to remove suspended matter or to enrich certain components. In general, however, the solution will still contain multiple components in addition to the mix of proteins that constitute the zein. Other solutes that may be present include, but are not limited to, starches, sugars, minerals, oil, fiber and protein or peptide fragments of various types. In general, the other solutes are of lower molecular weight than the zein components.

A further non-limiting goal of the process is to provide a more pure zein product by removing sugars from the solids in solution.

The solvent may be any solvent capable of dissolving zein, and may be a single simple solvent, or a solvent mixture or system. The solvent is usually, but not necessarily, non-aqueous, by which we mean that water is not usually the major component. Light alcohols, especially ethanol, are preferred as solvents or major components of a solvent mixture.

Zein proteins are essentially insoluble in pure water at neutral pH, but water may be, and typically is, a component of a solvent system. For example, mixtures of ethanol and water are known to provide a higher zein solubility than is provided by water or ethanol alone, and a 70/30 vol % ethanol/water mix is currently favored for its relatively high zein solubility by the corn processing industry.

Solutions containing other light alcohols, for example, isopropanol, may also be found from time to time.

Yet other possible solvent systems include aqueous systems that include surfactants or pH adjusting agents, for example.

The zein concentration in the raw feed solution may be any value. Typically, if the raw feed comes from an extraction step during corn processing, the zein content of the solution will likely be below 5 wt %, and frequently will be below 2 wt %.

The invention in its most basic embodiment comprises the following steps:
(a) providing a composite membrane having a feed side, a permeate side, and a dense, non-porous selective layer that is selective in favor of a solvent over zein;
(b) passing a feed solution comprising zein and the solvent across the feed side;
(c) withdrawing from the feed side a residue stream enriched in zein compared to the feed solution;
(d) withdrawing from the permeate side a permeate stream depleted in zein compared to the feed solution.

The membrane separation is filtration, that is, smaller components tend to permeate the membrane and larger components to be retained by the membrane. However, the process differs from traditional membrane filtration in that it uses a membrane with a separating layer that is dense, that is, non-porous. Although such membranes have been studied in the laboratory and reported in the literature, as mentioned in the Background section above, their use for the type of separations disclosed herein has not been suggested.

In principle, the membrane may take the form of a homogeneous film, an integral asymmetric membrane, a multilayer composite membrane, or any other form known in the art. Normally, however, the separating layer is extremely thin, so the preferred form for the membrane is a composite membrane including a microporous support layer for mechanical strength, coated directly or indirectly with a dense, non-porous polymer selective layer that is responsible for the separation properties.

If desired, the membrane may take the form of a multilayer composite membrane that includes additional layers besides the support layer and the selective layer. For example, a top layer may be coated onto the selective layer to seal any defects in the selective layer, and/or to discourage adhesion of proteins or other solute components on the membrane surface.

The microporous support membrane should have a flow resistance that is very small compared to the selective layer. The microporous support layer may be made from a polymeric material, an inorganic material, or any other suitable material. Preferred support membranes are asymmetric polymeric membranes, having a relatively open, porous substrate with a thin, finely porous skin layer. Polymers that may be used to form such a microporous support membrane include, but are not limited to, polysulfone, polyimide, polyvinylidene fluoride, polyamide, polypropylene or polytetrafluoroethylene. The support membrane may be reinforced by casting it on a fabric or paper web, made of polyester, for example.

The making of support membranes is well known in the art.

The selective layer is preferably made from a hydrophilic polymer. By hydrophilic, we mean that the polymer swells (as measured by its equilibrium percentage increase in weight) by at least about 15%, and preferably by at least about 20%, when immersed in water. In addition to facilitating permeation of polar solvents, the hydrophilicity of the membrane discourages hydrophobic solutes from adhering to the membrane surface, thereby ameliorating surface fouling problems.

Unlike traditional polymeric ultrafiltration membranes, the selective layer is a dense, non-porous polymer layer. By this, we mean that the layer is sufficiently free of pores and defects that transport of material through the membrane takes place primarily through the polymer itself. The absence of pores or defects in the selective layer may be determined by testing the gas permeation properties of a stamp of the membrane using air, for example.

When tested with an air mixture, a microporous membrane, such as is traditionally used for ultrafiltration, exhibits essentially no discriminating capability for oxygen over nitrogen, since both gases can pass readily through the pores. A membrane with very fine pores, such as might be used for nanofiltration, may exhibit Knudsen flow and a minimal selectivity (less than about 1.1) in favor of oxygen over nitrogen.

The membranes used in the present process, which rely on transport by solution/diffusion through the polymer phase, exhibit a higher selectivity for oxygen over nitrogen. The actual numerical value depends on the specific polymer and the extent to which the surface layer is free of cracks or other defects. If the membrane exhibits a selectivity of at least 1.2, more preferably at least 1.3 and most preferably at least 1.5, the membrane is considered to meet the dense, non-porous criterion.

Diverse hydrophilic polymers are known and may be used as preferred polymers to form the selective layer so long as they can be prepared in the form of a non-porous coating. Also preferred are polymers that include an ether segment, and more preferred are those that include both an ether segment and a hydrophilic segment.

Block copolymers incorporating both hydrophilic and hydrophobic segments are preferred in many cases because the copolymer presents a heterogenous surface of hydrophilic and hydrophobic patches to the feed solution, discouraging the conformational changes necessary for adherence of proteins to the surface.

The most preferred membrane materials are polyamide-polyether block copolymers having a chemical structure including aliphatic polyamide (PA) segments such as Nylon-6 and Nylon-12, and polyether (PE) segments such as polyethylene glycol, polypropylene glycol, or poly (tetramethylene ether glycol). The general formula for such structures is:

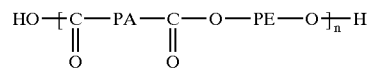

where PA is a polyamide segment, PE is a polyether segment and n is a positive integer.

The polyamide segment primarily determines the mechanical properties of the polymer and the polyether segment primarily determines the transport properties.

Polyamide-polyether block copolymers are commercially available in a variety of grades as Pebax® (Elf Atochem, Inc., Philadelphia, Pa.) or as Vestamid® (Nuodex Inc., Piscataway, N.J.). An increase in the polyether content of the copolymer increases the hydrophilicity, which results in higher water fluxes and better fouling resistance, but also lower organic solute rejection. The most hydrophilic grades currently available, Pebax® 1074 and Pebax® 1657 (formerly 4011), are capable of absorbing large amounts of water, reportedly 50% and 120 wt % water, respectively; therefore these are the preferred grades for use in the process of the invention.

The preparation of composite membranes made from these types of materials is described in detail in U.S. Pat. No. 4,963,165, as mentioned above, incorporated herein by reference in its entirety.

Other examples of block copolymers that may be used are those incorporating polyethylene oxide ($C_2H_4O$) segments, in conjunction with polyamide, polyimide, polysulfone or other glassy segments to give mechanical strength and/or increased hydrophilicity to the polymer.

The non-porous membranes of the present invention provide a much greater surface for active filtration per unit area of membrane than traditional filtration membranes, because the entire membrane surface, not just the pore area, is available to transport the permeating components. A representative surface porosity for a traditional porous ultrafiltration membrane is about 1%. All permeating material has to pass through these pores. Therefore, the effective filtration area available in the membranes of the present invention is typically about two orders of magnitude greater than the corresponding area in a porous membrane. This also helps to reduce the formation of a fouling layer on the membrane surface.

The membranes may be manufactured as flat sheets, tubes, or fibers, and housed in any convenient module form, including spiral-wound modules, plate-and-frame modules and potted fiber or tubular modules. The making of all these types of membranes and modules is well known in the art. Flat-sheet membranes in spiral-wound modules are our most preferred choice. Since conventional polymeric materials are usually used for the membranes, they are relatively easy and inexpensive to prepare and to house in modules.

If desired, the membrane modules may be adapted by any means known in the art to control build up of a concentration polarization layer on the membrane surface. Such techniques are especially useful if it is anticipated that the feed solution to be processed will have a high zein concentration.

Non-limiting techniques of this kind include the use of spinning or vibrating units. One such preferred unit is available from New Logic Research, Inc., of Emeryville, Calif. under the name VSEP®. The VSEP system uses rapid vibration in a direction tangential to the membrane surface to create high shear forces, thereby dislodging solid material from the membrane surface and remixing it into the bulk solution.

Whatever their composition and structure, the membranes should preferably have a rejection of zein of at least about 70%, more preferably at least about 80%, and most preferably at least about 90% or greater. With the most preferred Pebax membranes, zein rejections of 95%, 99% or even higher may be obtained.

As mentioned above, other solutes commonly found in zein solutions tend to have lower molecular weights than zein. For example, most sugars have molecular weights below 2,000 dalton, and sugars commonly found in zein solutions tend to have molecular weights below 1,000 dalton.

For preference, therefore, the membranes should have a molecular weight cut-off that is low enough to provide high rejection of zein components, yet permits high levels of permeation of low molecular weight components. The smallest zein proteins typically have molecular weights roughly around 12,000. Therefore, it is most preferred if the membrane has a molecular weight cut off above about 1,000 or 2,000 and below about 12,000.

It will be appreciated by those of skill in the art that molecular weight cut-off is not an intrinsic property of the membranes, but is dependent on the solvent, the solutes and the operating conditions of the process. When we refer to molecular weight cut-off herein, we mean the molecular weight cut-off as measured under the process conditions.

The most preferred polyamide-polyether block copolymers, such as the Pebax polymers, contain a variety of grades that meet the above requirements.

Under suitable operating conditions, such membranes can typically provide a zein rejection averaged over the duration of the process of at least 80%, 90% or better in conjunction with a low total sugars rejection of no more than about 50%, 40% or 20% rejection.

In addition, under appropriate circumstances, we believe that some grades may exhibit molecular weight cut-offs above 12,000 dalton, enabling separation between the lightest and heaviest zein fractions to be made.

To provide high solvent flux, the selective layer should be very thin, preferably no more than about 5 $\mu$m thick, and more preferably no more than about 2 $\mu$m thick. When in operation, the membranes should preferably provide a pressure-normalized flux for the solvent, or at least the major component of the solvent, averaged over the process operating time, of at least about 0.05 L/m$^2$ ·h·psi.

The process of the invention in its most basic form is shown in FIG. 1. Referring to this figure, feed zein solution, 1, is passed into membrane separation unit, 2, and flows across the feed side of membrane, 3, which is characterized as described above. Under a pressure difference between the feed and permeate sides of the membrane, solvent and low molecular weight solute components pass preferentially to the permeate side, and permeate stream, 5, containing these components and depleted in zein, is withdrawn from the permeate side. The remaining liquid residue stream, 4, is withdrawn as zein-enriched retentate from the feed side.

A driving force for transmembrane permeation is provided by a pressure difference between the feed and permeate sides of the membrane. This is usually, but not necessarily, achieved by means of a pump in the membrane feed line. Increasing the pressure difference results in an increase in transmembrane flux of all components. At low pressure differences, this relationship is linear.

However, as the transmembrane pressure difference increases, the concentration of retained material carried by convection to the membrane surface increases, encouraging formation of a concentration polarization or gel layer on the feed side surface that provides an additional permeation resistance in series with the membrane. This additional resistance causes the transmembrane flux to level off, ultimately to the point that flux becomes independent of applied feed pressure.

As a further problem, the gel layer may provide greater rejection of the low molecular weight solutes than does the membrane. Therefore, as the gel layer increases in thickness and density, the rejection of the non-zein solids tends to increase.

As a result, high applied pressures tend both to exacerbate concentration polarization problems and to reduce the purity of the rejected zein product, and are neither required nor preferred. As a rough guide, the applied pressure on the feed side should preferably be no higher than about 150 psig for most processing applications. Most preferred operating pressures are lower, consistent with typical operating pressures for ultrafiltration, and are generally in the range about 50–150 psig.

Optionally, the feed solution may be warmed before it is introduced into the membrane separation unit. Warming increases the solubility of the solutes and discourages gel formation on the membrane surface. Zein proteins begin to degrade at around 50° C., so preferred temperatures to which the solution may be warmed are lower than this, generally up to about 35° C.

Warming is particularly helpful for feed solutions of relatively high solute concentration, such as may be found in the later steps of a multistep chain of concentration units, or toward the end of the cycle time in a batch or loop process.

Membrane separation unit 2 may contain a single membrane module or bank of membrane modules, or may be a more complicated multistep or multistage unit. For example, residue or retentate stream 4 from the first membrane step may be passed to a second module or bank of modules for further concentration. A chain of two, three or even more processing steps or units in series in this manner is commonly used.

Less commonly, permeate stream 5 from the first stage might be passed to a second module or bank of modules to recapture zein lost to the permeate in the first processing step.

The process may be carried out as a continuous or a batch process, and according to any convenient operating mode, such as single-pass, partial recirculation, or full recirculation.

In general, the process should aim to reduce the volume of zein-containing solution that forms the retentate withdrawn at the end of the process to no more than about 30 vol %, 20 vol % or even 10 vol % of the raw feed volume. This degree of concentration corresponds to a solids concentration in the recovered is of between about five and ten times higher than that of the feed.

In principle, both for simplicity, and to avoid subjecting any shear-sensitive components to repeated pumping, operation of the process in continuous, single-pass mode is desirable. However, if the feed solution is progressively reduced to 30%, 20%, 10% or less of its original volume, this typically requires a relatively complicated "Christmas tree" array of membrane modules to keep fluid flow velocity high as flow volume decreases.

On the other hand, full recirculation of the residue stream to the feed inlet, so that the process is operated on the feed side in a closed loop batch mode, can create a high total solids concentration in the solution on the feed side, especially if circulation is continued for a prolonged period. However, this type of operation may lead progressively to formation of a zein gel layer on the membrane surface, which in turn may lead to loss of performance by the membrane, as discussed above.

Processing to the point at which the total solids concentration on the feed side of the membrane rises above about 20 wt % is not preferred, and more preferably the total solids concentration on the feed side should not be allowed to rise above about 10 wt %.

More preferred than either of the above modes, therefore, is to operate in a partial recycle, commonly known as feed-and-bleed, mode. In this manner, a feed stream can be introduced to the process continuously, and a residue stream withdrawn continuously. A portion of the residue stream is recirculated, as indicated by dashed line 6 in FIG. 1, to build up the solute concentration in the loop to the desired value.

The operation of filtration systems in feed-and-bleed and other specific modes such as those discussed above is known in the industry. If required, more details of various operating modes, and the effect of their operating parameters on processing results, may be found in Chapter 7 of M. Cheryan, Ultrafiltration and Microfiltration Handbook (Technomic Publishing Company, Inc, Lancaster, Pa., 1998).

Figure 27:
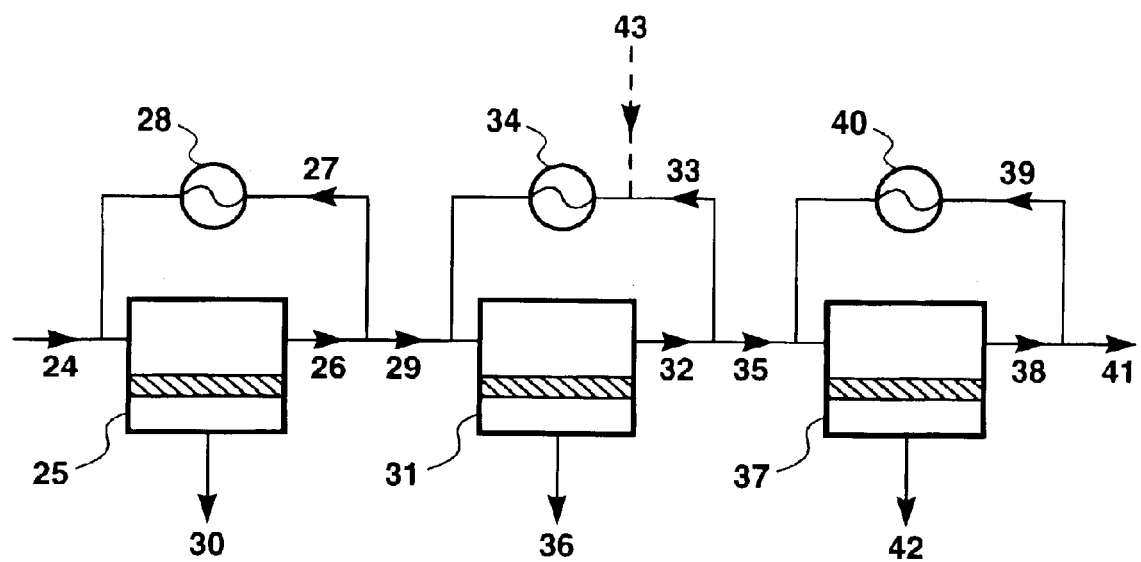
FIG. 27 is a flow diagram showing a typical arrangement of the process of the invention having three feed-and-bleed units arranged in series.

By way of representative example, FIG. 27 shows a typical arrangement of feed-and-bleed units arranged in series. Feed zein solution, 24, is passed into first membrane separation unit, 25, where it is separated into zein-enriched residue stream, 26, and permeate solvent stream, 30. A portion, 27, of stream 26 is recirculated through the membrane separation unit by pump, 28.

Bleed stream, 29, is withdrawn from the processing loop of unit 25 and passed as second feed solution to the second membrane separation unit, 31. This second feed solution is relatively rich in zein and poor in sugars compared with initial feed solution 24. The second unit separates its feed solution into second zein-enriched residue stream, 32, and second permeate solvent stream, 36. A portion, 33, of stream 32 is recirculated through the second membrane separation unit by pump, 34.

Bleed stream, 35, is withdrawn from the processing loop of unit 31 and passed as the third feed solution to third membrane separation unit, 37. The third feed solution, 35, is proportionately richer in zein and leaner in sugars than second feed solution 29. This third unit produces third zein-enriched residue stream, 38, and third permeate solvent stream, 42. A portion, 39, of stream 38 is recirculated through the third membrane separation unit by pump, 40. Bleed stream, 41, is withdrawn from the processing loop of unit 37 and is withdrawn as the zein-rich concentrate or retentate product.

Permeates 30, 36 and 42 may be disposed of as desired. Typically, they might be sent to another treatment for sugar removal and reused as solvent in upstream operations.

In light of the factors discussed above, and whichever operating mode is chosen, the zein concentration of the withdrawn residue stream should preferably be between about five and ten times higher than that of the feed. A typical increase in concentration might be from 1.2 wt % to 7 wt %, for example.

The total dissolved solids content of the residue will normally be made up of zein and other components. With respect to zein and sugar, for example, the withdrawn residue stream will contain proportionately more zein and less sugar compared with the feed stream, because the membrane exhibits high rejection of zein and lower rejection of sugars.

The zein purity, by which we mean the weight of zein solids in the residue stream as a percentage of the total solids in the residue stream, should generally be as high as possible.

A preferred way to increase zein purity while controlling concentration polarization is to use diafiltration. Diafiltration refers to the process of diluting the retentate by adding additional solvent and repeating or continuing the filtration process. Dilution reduces the total solids concentration on the feed side of the membrane, thereby avoiding or at least ameliorating gel layer formation; continued processing provides further reduction of the small, preferentially permeating solutes. In this way, the relative proportions of, say, zein to sugar, are increased, that is, the zein purity is increased.

Diafiltration may be carried out batchwise. In other words, the process is run in any mode for a period of time, and the residue stream is collected. The collected residue is then diluted, typically, but not necessarily, back to the original total solids concentration, and the resulting liquid is reprocessed. The collection/dilution/reprocessing steps may be repeated as desired until a target zein concentration is achieved.

More preferable, if convenient, is to use continuous diafiltration, which is carried out by continuously adding solvent to the solution circulating on the feed side. As a non-limiting example, with reference to FIG. 27, each membrane separation unit might reduce the treated solution volume to 40% of its original value. That is, stream 29 has a flow 40% that of stream 24, stream 35 has a flow 40% that of stream 29, and stream 41 has a flow 40% that of stream 35. Overall, the three-step process of FIG. 27 would then reduce the solution volume to about 6% of its original value, that is, by about 94%.

At this point, a substantial gel layer might have formed, causing sugar rejection to rise and transmembrane flux to drop. This problem could be controlled by adding diluting solvent during the second processing step, as indicated by dashed line 43 in FIG. 27. This would keep flux higher and sugar rejection lower in this step, thereby increasing zein purity. The third step could then be used to concentrate the purified zein solution to the desired level.

As a general guideline, a preferred point to introduce diluting solution is when the solution flow volume has been reduced by approaching, but no more than, about 70% or 80%.

Optionally, the diluting solvent may be added at the same rate as the permeate flux. In this case, the feed volume remains constant during processing as the zein purity increases. When the desired purity has been obtained, the solution may be concentrated by running without dilution.

Operation in continuous mode results in a continuous supply of purified retentate, but requires a relatively large supply of solvent and proportionately larger pumps to handle the feed and permeate solutions.

The solvent used as diluent may be the same as the original solvent or may be different. For example, if the original solvent is an ethanol/water mix, the composition may be changed to reduce or eliminate the water content in the final concentration steps. This may make it easier to use evaporation to recover a dried zein product, if desired.

So long as the non-zein solutes present in the feed solution are less well rejected than zein, it is possible to achieve any desired level of zein purity in the retentate solids fraction, such as 70%, 80%, 90%, 95%, 99% or greater purity, by continuing diafiltration until essentially no other solutes remain.

The permeate stream from the membrane separation step typically contains all components of the solvent system, as well as sugars and other low-molecular-weight solutes that were present in the feed solution. Since the membranes provide good rejection of zein, zein losses into the permeate are usually small, and are typically no more than a few percent, such as 10 wt %, 5 wt %, 2 wt % or less of the zein content of the feed.

The membranes are not perfectly impermeable to zein. If diafiltration is used, the longer it is continued, the more zein will be lost into the permeate. The balance between high zein purity in the retentate and low zein loss into the permeate can be made based on specific needs.

The permeate stream may pass to any desired destination. For example, if the permeate is rich in sugars, it may be passed to a fermentor for ethanol production. It may be added to the beer still if one is available. Another option is to treat the permeate to remove other solutes, then reuse the solvent for extraction or other purposes.

The protein-enriched residue stream is optionally, but not necessarily, sent for further concentration or processing to recover a purified zein product. Typically it may be sent to a spray dryer, for example.

Another recovery option is to send the stream first to an evaporator for further concentration and then to a spray dryer.

The ability of the process to provide such a high degree of solvent reduction is particularly beneficial with respect to any such downstream operations. For example, if the volume flow of feed solution to be subjected to spray drying is only 20% or 10% of the original feed solution volume flow, the capacity and energy requirements for the spray drying step are correspondingly reduced.

Figure 26:
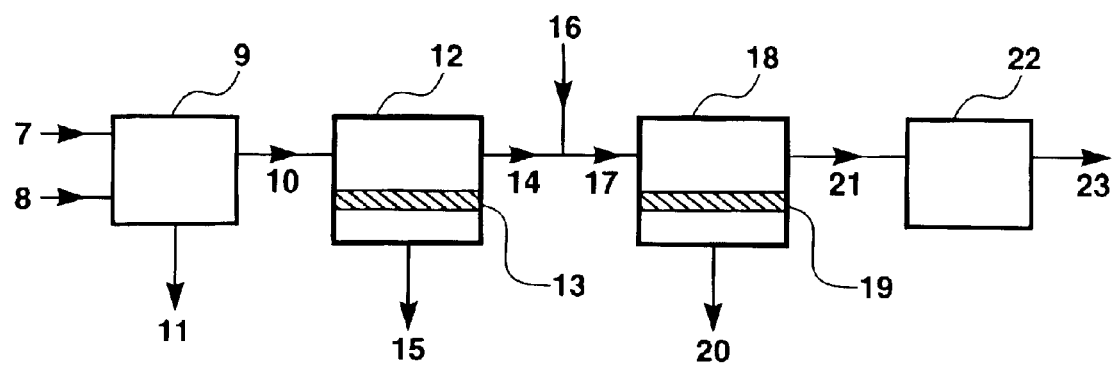
FIG. 26 is a flow diagram showing a representative scheme for zein production.

As will be apparent to those of skill in the art, many opportunities for making use of the process of the invention exist. FIG. 26 shows a non-limiting, representative scheme in which a two-step membrane separation process with in-line diafiltration is used as part of a zein production operation. FIG. 26 is a basic flow diagram; any other steps may be included as appropriate between the steps shown.

Referring to this figure, zein-containing feed 7 and solvent 8 are brought into contact, and zein is extracted in solvent extraction step, 9, yielding raw zein solution, 10. Remaining materials from the zein-containing feed left after the extraction step are indicated by stream 11.

After any other treatment as required, such as to remove suspended matter, stream 10 passes as feed solution to first membrane separation step, 12, equipped with dense, non-porous filtration membranes, 13, as described above. Step 12 may be carried out in any operating mode until the solids concentration in residue stream, 14, reaches a desired value. Permeate solvent stream, 15, is withdrawn.

Residue stream 14 is diluted with additional solvent, stream 16, to form diluted stream, 17. Stream 17 passes as feed solution to second membrane separation step, 18, equipped with dense, non-porous filtration membranes, 19, as described above. Step 18 may again be carried out in any operating mode until the solids concentration in residue stream, 21, reaches a desired value. Permeate solvent stream, 20, is withdrawn.

Zein-rich concentrate stream 21 is withdrawn and sent to purification step, 22, which is typically performed by spray-drying, evaporation, or evaporation followed by spray drying. Purified zein product, typically in powder form, is recovered as stream 23.

The invention is now further described by the following examples, which are intended to be illustrative of the invention, but are not intended to limit the scope or underlying principles in any way.

EXAMPLES

Example 1

Membrane Preparation

Composite membranes were made from both Pebax® 1074 and Pebax® 1657 grades (Elf Atochem, Philadelphia, Pa.) in a two-step process. First, a microporous support layer of polyvinylidene fluoride (PVDF) was cast onto a fabric web. In the second step, the support layer was coated with a dilute Pebax® solution. After drying in an oven, a selective layer 0.5–2 $\mu$m thick was left on the support.

Stamps of each membrane were cut and the gas permeation properties measured. The 1074 grade membrane stamps had oxygen/nitrogen selectivity ranging from 2.1 to 2.7. The 1657 grade membranes had oxygen/nitrogen selectivity ranging from 2.0 to 2.7.

Example 2

Membrane Stamp Solvent Permeation Tests

Samples of membranes prepared as in Example 1 were cut into 9.6 cm$^2$ stamps and mounted in a permeation system containing a stirred test cell.

Pure ethanol was introduced into the cell, and the ethanol flux was measured at a feed pressure of 50 psig and a feed temperature of 32° C. The membrane stamp had a pure ethanol pressure-normalized flux of 0.26 L/m$^2$ ·h·psi.

The experiment was repeated using a solvent mixture of 70 vol % ethanol/30 vol % water, again at a feed pressure of 50 psig and a feed temperature of 32° C. The membrane had a pressure-normalized flux for the solvent mixture of 0.36 L/m$^2$·h·psi.

Example 3

Membrane Stamp Zein Permeation Data

The flux and rejection properties of membranes made from Pebax grades 1074 and 1657 were compared. Membranes were made from each grade of polymer following the procedure described in Example 1. Membrane samples were cut into 9.6 cm$^2$ stamps and mounted in a test cell.

For each experiment, the membrane was contacted with 250 mL of zein solution. The solution contained 0.6 wt % high purity zein dissolved in a solvent mixture of 85 vol % ethanol/15 vol % water. The cell was pressurized to 400 psig, and flux measurements were made at room temperature (21° C.). Permeate samples of 5 g each were collected for analysis, along with samples of the feed and the final retentate. Zein content was determined by the Dumas combustion method. Samples were dried in an 80° C. oven for 2 hours to evaporate the solvent. Nitrogen (N) was determined using a Leco FP-528 protein/nitrogen analyzer (Leco, St. Joseph, Mich.). Protein content is expressed as N×6.25.

Typical results of the experiment are shown in Table 1.

TABLE 1

| Membrane | Pressure-Normalized Flux $(L/m^2 \cdot h \cdot psi)$ | Zein Rejection (%) |
| --- | --- | --- |
| Pebax ® 1074 | 0.029 | 92.0 |
| Pebax ® 1657 | 0.024 | 92.7 |

Either polymer grade was able to provide good zein rejection. High feed pressure, and hence formation of a relatively thick gel layer on the membrane, likely contributed to the low pressure-normalized fluxes.

Examples 4–14

Membrane Module Permeation Data

Example 4

Water Flux

Membranes with a Pebax® 1074 selective layer were prepared as in Example 1 and rolled into 2.5-inch-diameter spiral-wound modules with a membrane area of about 1.5 $m^2$. A module was mounted in a bench-top test system equipped with a 40-L feed tank and recirculation loops allowing the residue stream, and optionally the permeate stream, to be returned to the feed tank.

Figure 2:
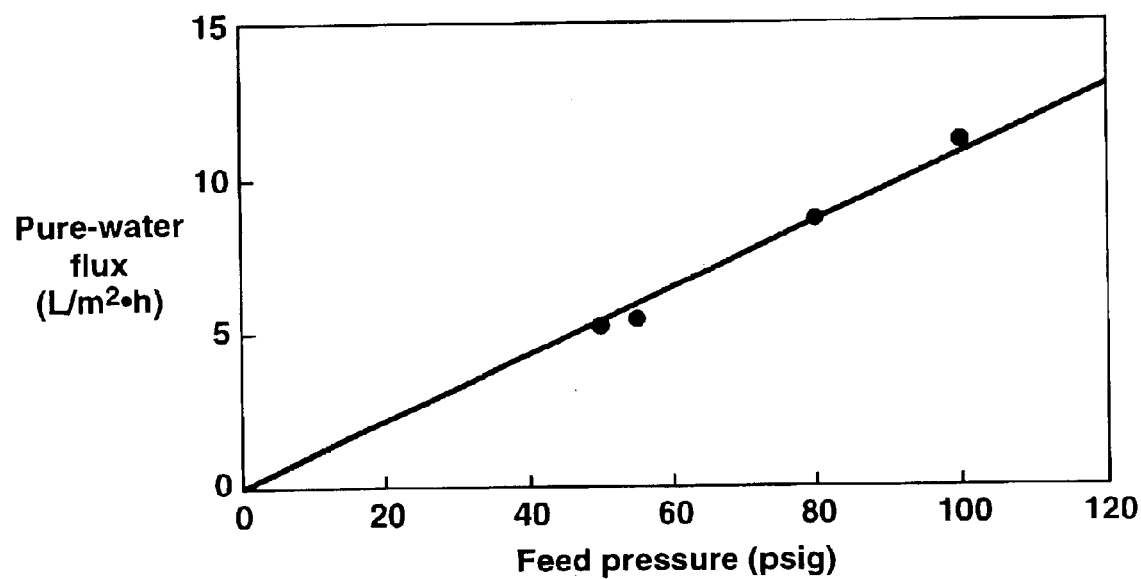
FIG. 2 is a graph showing pure water flux as a function of feed pressure for a spiral-wound module incorporating a non-porous Pebax® 1074 membrane.

Pure water was circulated through the system at a flow rate of 3 gpm. The permeate water flux of the module was measured at feed pressures of 50, 80, and 100 psig at 23° C. feed temperature. FIG. 2 shows the pure water flux as a function of feed pressure.

Example 5

Solvent Flux

Figure 3:
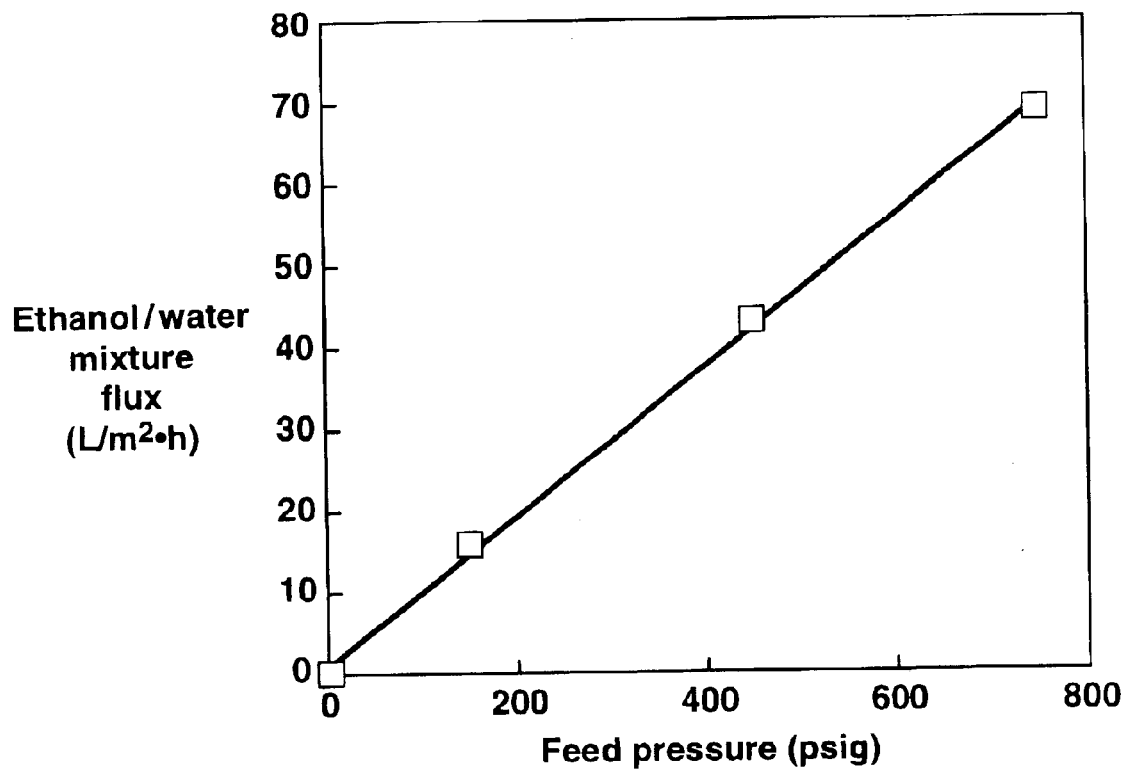
FIG. 3 is a graph showing solvent flux as a function of feed pressure for a solvent mixture of 70 vol % ethanol/30 vol % water using a spiral-wound module incorporating a non-porous Pebax® 1074 membrane.

Pebax® 1074 module prepared as in Example 4 was tested with a solvent mixture of 70 vol % ethanol/30 vol % water at feed pressures of 150, 450 and 750 psig at 23° C. feed temperature. FIG. 3 shows the solvent flux as a function of feed pressure.

Example 6

Zein Rejection

The membrane module used in Example 4 was used to test zein rejection in the bench-top system. The initial feed was a solution of 70 vol % ethanol/30 vol % water containing 1.7 wt % total dissolved solids. The feed pressure was maintained at 150 psig and the feed temperature was maintained at 28° C. Feed solution was circulated through the module at a flow rate of 1 gpm. The permeate stream was not recirculated to the feed tank, so that the feed concentration increased over time. The results are shown in Table 2.

TABLE 2

| Time of Operation | Total Solids Concentration (wt %) | | Pressure-Normalized Flux | Total Solids Rejection | Zein Rejection |
| --- | --- | --- | --- | --- | --- |
| (min) | Feed | Permeate | $(L/m^2 \cdot h \cdot psi)$ | (%) | (%) |
| 0 | 1.7 | 1.0 | 0.07 | 40 | 83 |
| 15 | 2.4 | 1.2 | 0.07 | 50 | >99 |
| 30 | 2.0 | 1.0 | 0.06 | 50 | >99 |
| 45 | 2.1 | 1.0 | 0.06 | 52 | >99 |

In general, the pressure-normalized fluxes were lower than those obtained with the corresponding membrane stamps, possibly due to higher stage-cut (fraction of feed permeating the membrane) in the module tests.

A zein mass balance calculation showed that some protein was being retained in the module and the system. However, the permeate flux was constant over time, suggesting that gel formation on the membrane surface is not a significant problem.

The low zein rejection measured initially is likely to be a start-up artifact.

Example 7

Pilot Plant Test

Membrane modules prepared as in Example 4 were tested at a facility in Saskatoon, Canada (POS Pilot Plant), operated by PSI Process Systems, Inc. of Memphis, Tenn. The facility was equipped with analytical capabilities including HPLC, NMR, GC, capillary electrophoresis, and chemical titration kits for characterization of process streams.

The tests were conducted using a high-pressure pilot system capable of holding two membrane modules in a series or parallel configuration. The feed pressure in the system could be varied up to 1,000 psig and the solution flow rate could be varied up to 10 gpm.

The feed solution was 500 L of a zein extract solution containing 3 wt % total dissolved solids of which the zein concentration was 1.2 wt % (40 wt % of total solids), and the rest was made up of sugars and flavor compounds. The solvent mixture was 80 vol % ethanol/20 vol % water. The solution had been pretreated to remove suspended matter and other components.

The membrane concentration step was carried out in batch mode. At the end of each batch treatment, the retentate tank connections were switched with the feed tank and the concentration operation continued. The feed pressure was maintained at 200 psig, the feed temperature was maintained at 25° C., and the feed solution flow rate was 2.2 gpm.

Figure 4:
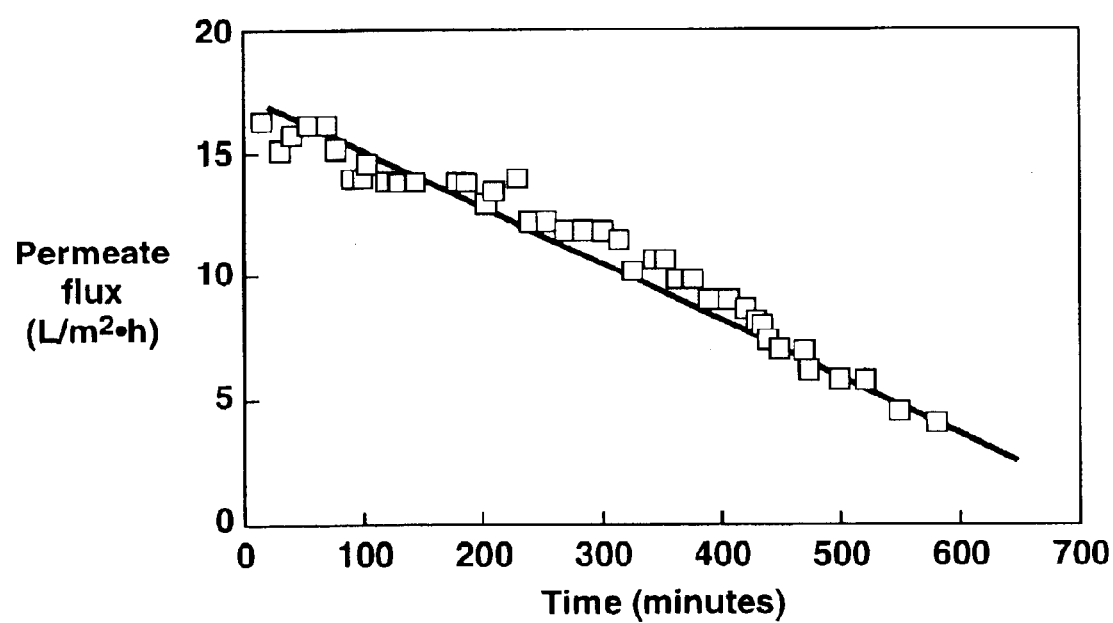
FIG. 4 is a graph of total flux as a function of processing time for a spiral-wound module incorporating a non-porous Pebax® 1074 membrane treating a feed solution of 3 wt % total dissolved solids initial content in a solvent mixture of 80 vol % ethanol/20 vol % water.
Figure 5:
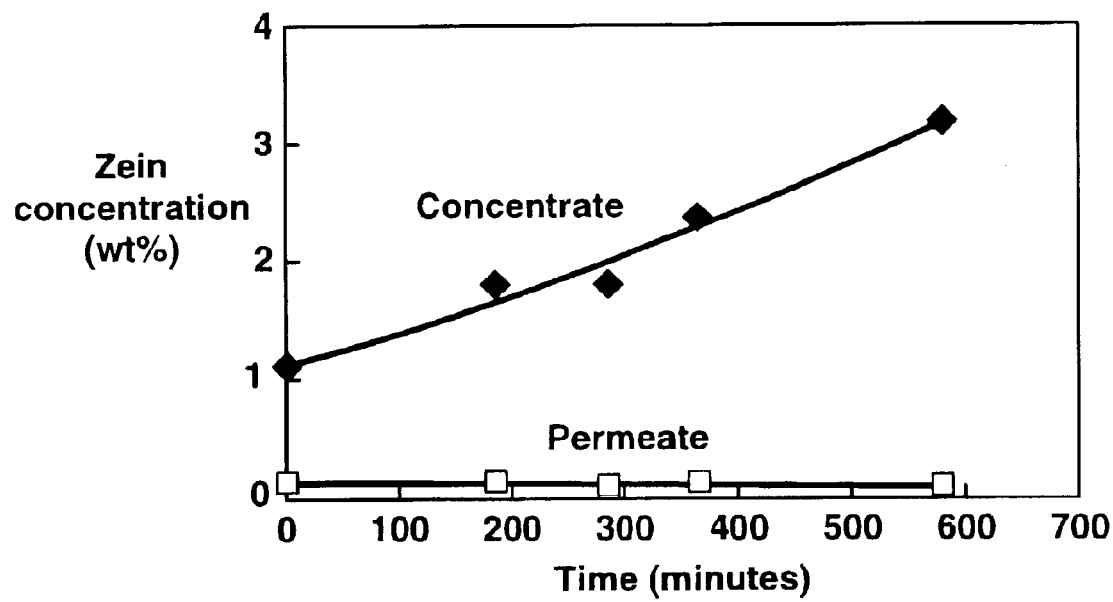
FIG. 5 is a graph showing zein concentration in the retentate and permeate as a function of processing time for a spiral-wound module incorporating a non-porous Pebax® 1074 membrane treating a feed solution of 3 wt % total dissolved solids initial content in a solvent mixture of 80 vol % ethanol/20 vol % water.
Figure 6:
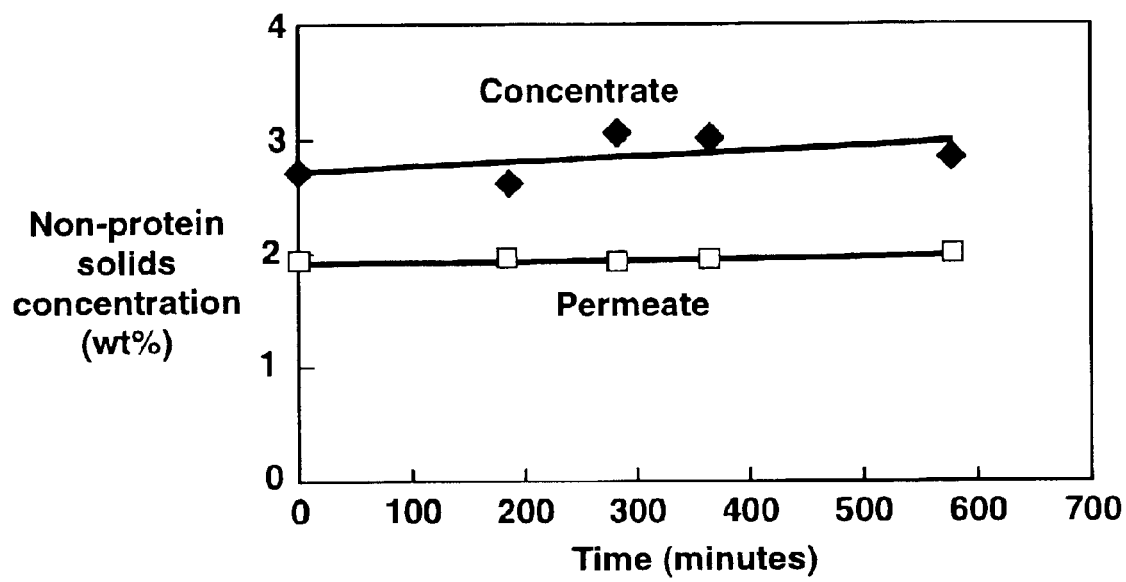
FIG. 6 is a graph showing non-protein solids concentration in the retentate and permeate as a function of processing time for a spiral-wound module incorporating a non-porous Pebax® 1074 membrane treating a feed solution of 3 wt % total dissolved solids in a solvent mixture of 80 vol % ethanol/20 vol % water.

FIGS. 4–6 show the permeate flux, the zein concentration, and the non-protein solids concentration as a function of processing time.

As can be seen, the total permeate flux decreased overtime as the solids concentration on the feed side increased, leading to progressive gelling of the zein and increasing viscosity of the concentrate.

The zein concentration on the feed side continued to increase throughout the experiment, indicating good zein rejection. On the other hand, the concentration of non-protein solids remained nearly constant over time, indicating low rejection of these components.

Figure 7:
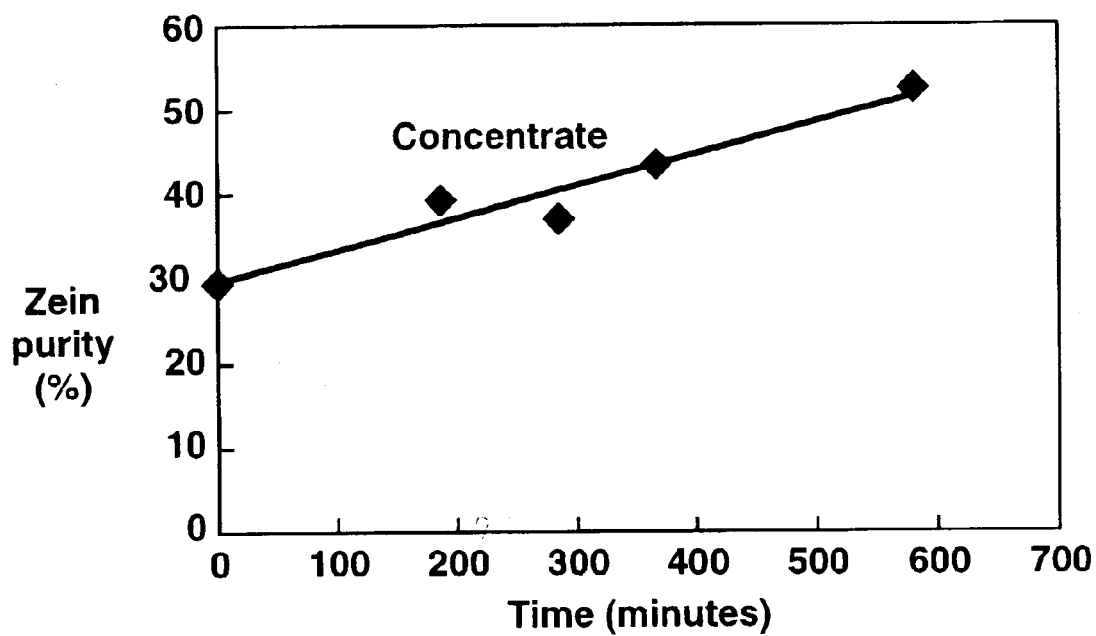
FIG. 7 is a graph showing the increase over time of zein content as a percentage of total dissolved solids content in the retentate based on the data shown in FIGS. 5 and 6.

Since non-zein solids were transported readily to the permeate side whereas zein solids were rejected, the zein purity (zein content of the total solids in the retentate) increased from 30 wt % to more than 50 wt %, as shown in FIG. 7.

Figure 8:
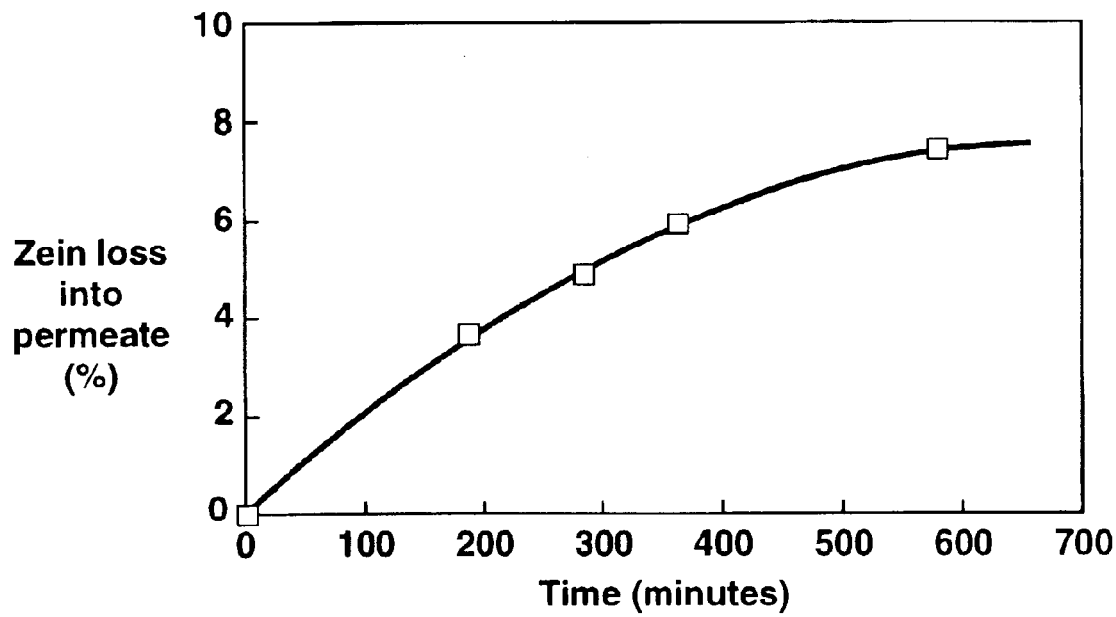
FIG. 8 is a graph showing zein loss into the permeate over time based on the data shown in FIGS. 5 and 6.

Overall zein loss into the permeate was less than 8 wt %, as shown in FIG. 8.

Example 8

Dilute Solution Test

A sample of zein extract was diluted 10-fold with a 70 vol % ethanol/30 vol % water solution to make 40 L of feed solution with a total dissolved solids concentration of 0.17 wt %. At this low solids concentration, gelation of the feed solution was not expected to occur.

A membrane module prepared as in Example 4 was tested with the diluted solution. The solution was circulated through the module test system. Both residue and permeate streams were recirculated within the processing loop to maintain a dilute feed concentration throughout the experiment. The feed pressure was increased from 25 to 80 psig, the temperature was maintained at 25° C., and the feed solution flow rate was 3 gpm. The total permeate flux was measured and the rejection calculated.

Figure 9:
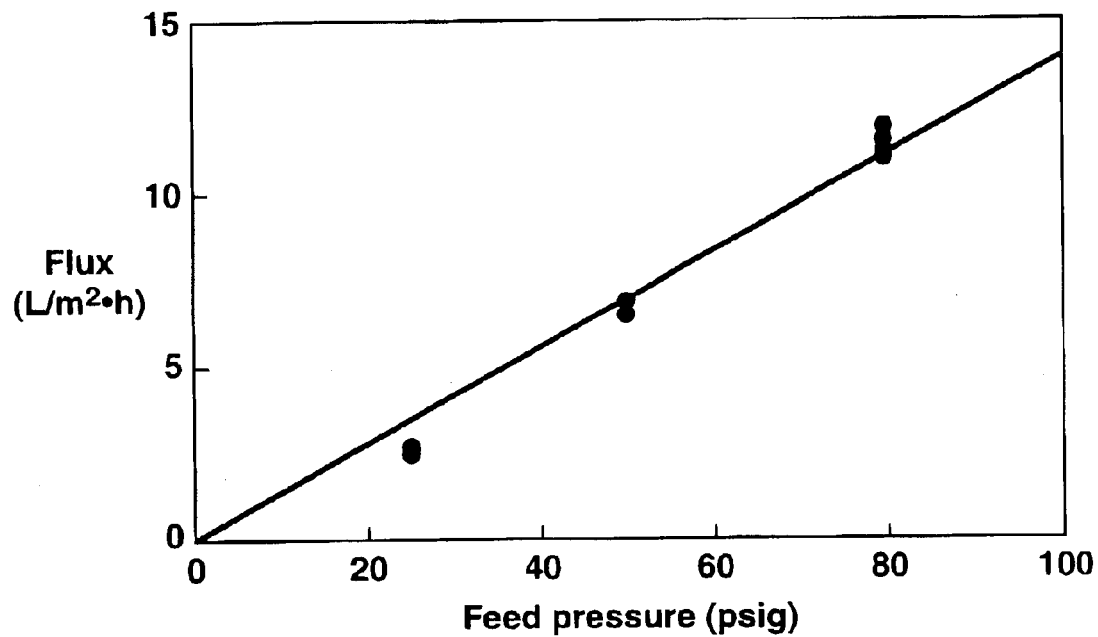
FIG. 9 is a graph showing total flux as a function of feed pressure for a spiral-wound module incorporating a non-porous Pebax® 1074 membrane treating a feed solution of 0.17 wt % total dissolved solids in a solvent mixture of 70 vol % ethanol/30 vol % water.

FIG. 9 is a graph showing the total flux as a function of feed pressure. As can be seen, the flux increases linearly with increasing feed pressure, consistent with absence of resistance from a gel layer on the membrane surface.

The average total dissolved solids concentrations in the feed and permeate were 0.17 wt % and 0.10 wt %, respectively. From these concentrations, the total solids rejection was calculated to be 41%. The extract was not analyzed to determine the zein and sugar proportions. However, an overall solids rejection of 41% is consistent with a high zein and low sugar rejection.

Example 9

Short-term Feed Concentration Test—Dilute Solution

The experiment of Example 8 was repeated, except that the permeate was withdrawn rather than recycled to the feed tank, so that the solids concentration on the feed side increased over time. The feed pressure was maintained at 80 psig, the temperature was maintained at 25° C., and the feed solution flow rate was 3 gpm. After one hour of operation, the feed concentration had increased 40%, from 0.17 wt % to 0.24 wt %. The pressure-normalized flux remained constant at 0.12 L/m² ·h·psi, indicating no membrane fouling. The total dissolved solids concentration in the permeate was stable at 0.08 wt %.

Example 10

Undiluted Solution Test

Figure 10:
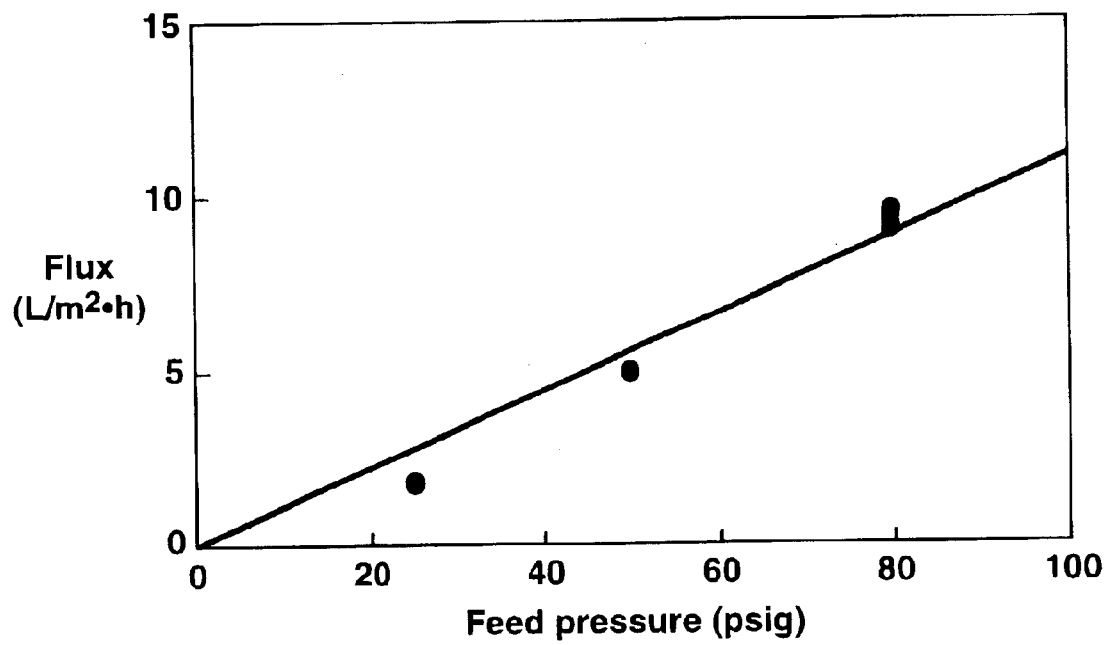
FIG. 10 is a graph showing total flux as a function of feed pressure for a spiral-wound module incorporating a non-porous Pebax® 1074 membrane treating a feed solution of 1.7 wt % total dissolved solids in a solvent mixture of 70 vol % ethanol/30 vol % water.

The experiment of Example 8 was repeated with undiluted zein extract having a total solids concentration of 1.7 wt %. The permeate was again recycled to the feed tank to maintain the same zein concentration throughout the experiment. The feed pressure was increased from 25 to 80 psig, the temperature was maintained at 25° C., and the crossflow rate was 3 gpm. The fluxes were measured and the rejections calculated. FIG. 10 shows the flux results.

As was seen with the dilute feed in Example 8, the flux increased linearly with increasing feed pressure. The average total dissolved solids concentrations in the feed and permeate were 1.7 wt % and 0.9 wt %, respectively. The total solids rejection was 47%.

Example 11

Short-term Feed Concentration Test—Undiluted Solution

The experiment of Example 9 was repeated with the undiluted solution of Example 10. After 90 minutes of operation, the feed concentration had increased 20%, from 1.7 wt % to 2.0 wt %. The pressure-normalized flux remained constant at 0.12 L/m² ·h·psi.

Example 12

Long-term Feed Concentration Test—Undiluted Solution

The experiment of Example 11 was repeated and continued for a three-day period. The feed pressure was maintained at 80 psig, the temperature was maintained at 25° C., and the feed solution flow rate was 3 gpm. After three days, the feed concentration had increased three-and-a-half-fold, from 1.7 wt % to 6.0 wt %.

Figure 11:
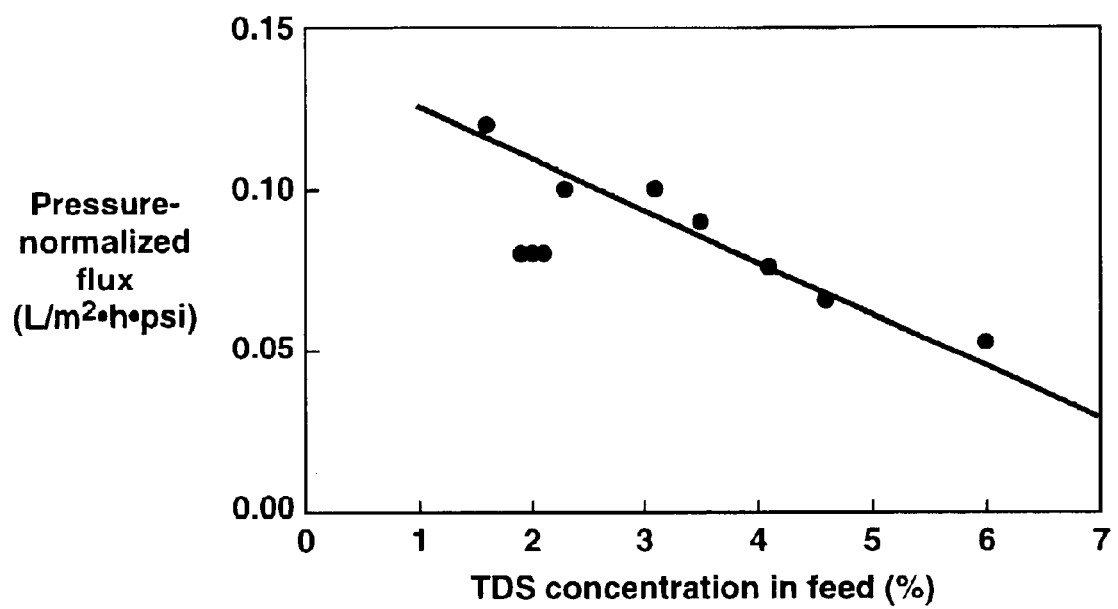
FIG. 11 is a graph of pressure-normalized flux as a function of total dissolved solids concentration in the feed solution for a spiral-wound module incorporating a non-porous Pebax® 1074 membrane treating a feed solution of 1.7 wt % total dissolved solids initial content in a solvent mixture of 70 vol % ethanol/30 vol % water.

As seen in FIG. 11, the pressure-normalized flux declined from about 0.12 L/m² ·h·psi to about 0.05 L/m² ·h·psi as the feed concentration increased.

Figure 12:
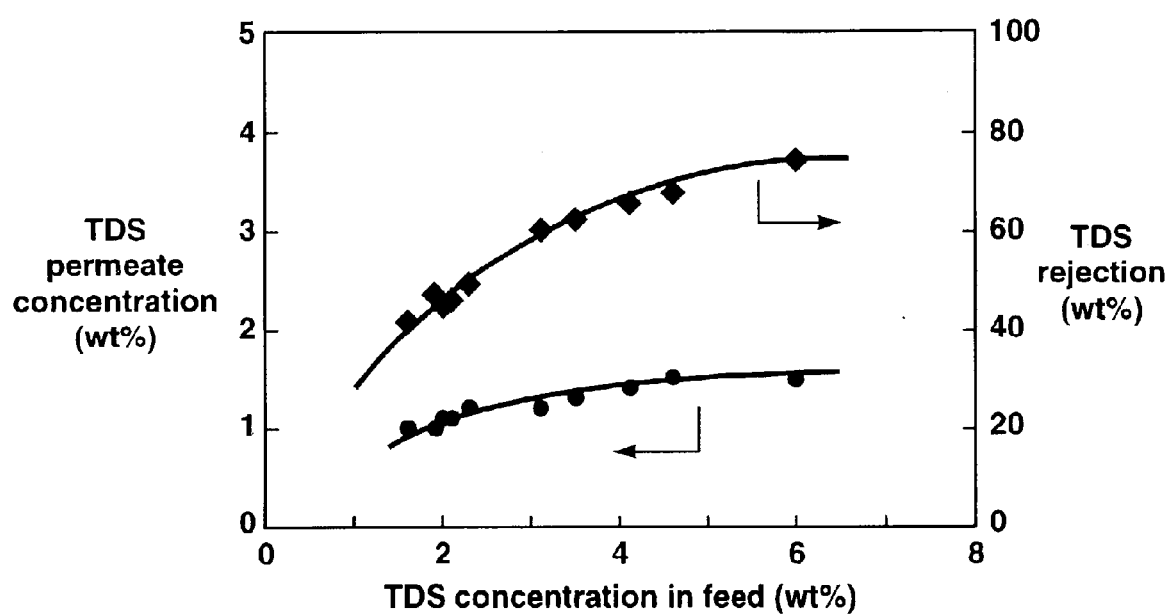
FIG. 12 is a graph showing total dissolved solids rejection and total dissolved solids concentration in the permeate as a function of total dissolved solids concentration in the feed solution for a spiral-wound module incorporating a non-porous Pebax® 1074 membrane treating a feed solution of 1.7 wt % total dissolved solids initial content in a solvent mixture of 70 vol % ethanol/30 vol % water.

As shown in FIG. 12, both the total dissolved solids concentration in the permeate and the total dissolved solids rejection increased as the feed concentration increased.

Example 13

Feed Concentration Test Comparison of Experimental Data with Theoretical Concentration Curves A concentration experiment was carried out using the same module and operating conditions as in Examples 11 and 12 to concentrate a 40-L batch of feed solution in a solvent mixture of 70 vol % ethanol/30 vol % water from an initial 2.7 wt % total dissolved solids to 5.6 wt % total dissolved solids. The increase in concentration was achieved by permeating 76 vol % of the feed.

The feed and permeate solutions were sampled from time to time and the total dissolved solids concentrations in the feed and permeate were measured.

Figure 13:
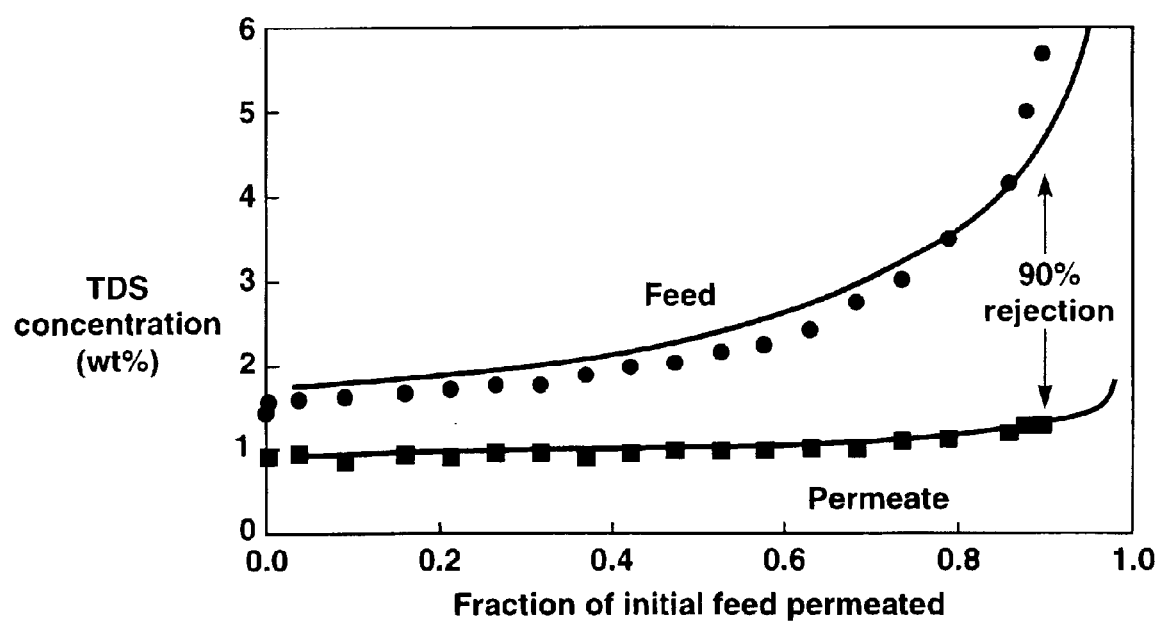
FIG. 13 shows the total dissolved solids concentrations in the feed and permeate as a function of the fraction of initial feed permeated. The figure also shows calculated concentration curves assuming 90% zein rejection and no sugar rejection by the membrane.

FIG. 13 shows the experimental data points. The total solids concentration in the permeate remained low throughout the experiment. FIG. 13 also shows concentration curves calculated assuming that zein rejection is 90% and that sugar is not rejected. As can be seen, the data points correlate well with the calculated curves.

Figure 14:
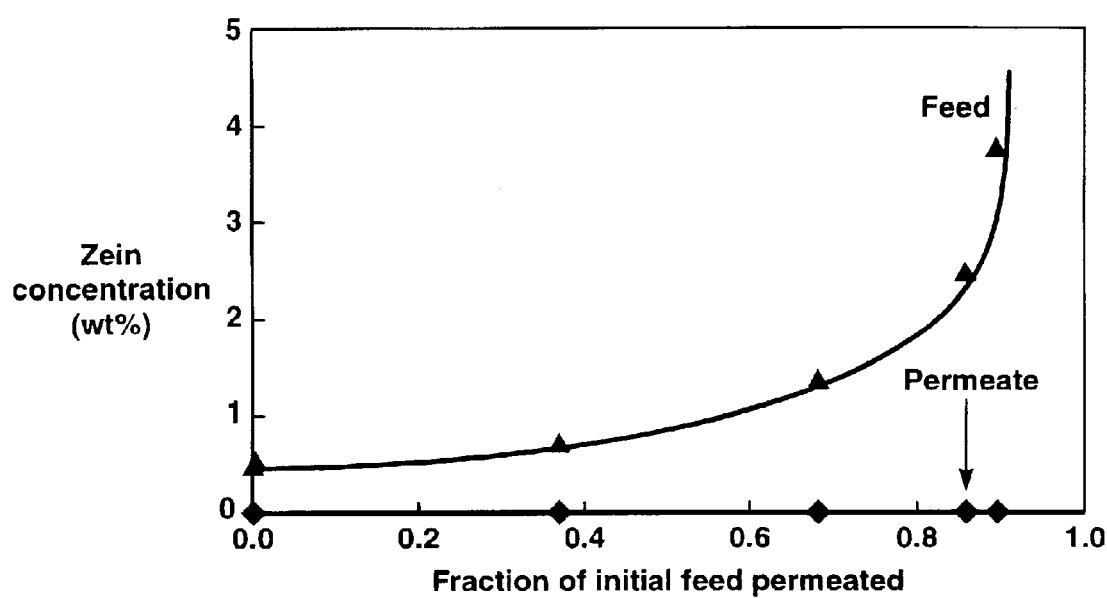
FIG. 14 is a graph showing the zein concentrations in the feed and the permeate for the same experiment as FIG. 13.

Feed and permeate samples were sent to the University of Illinois at Urbana-Champaign, where the zein content was determined by matrix-assisted laser desorption ionization mass spectroscopy (MALDI-MS). FIG. 14 shows the zein concentration in the feed and the permeate as revealed by this analysis.

As can be seen, the zein concentration in the feed increased very substantially as processing continued. The zein concentration in the permeate remained almost negligibly small throughout the experiment. The results were found to be consistent with a zein rejection of at least 99%, much greater than the predicted 90%.

Figure 15:
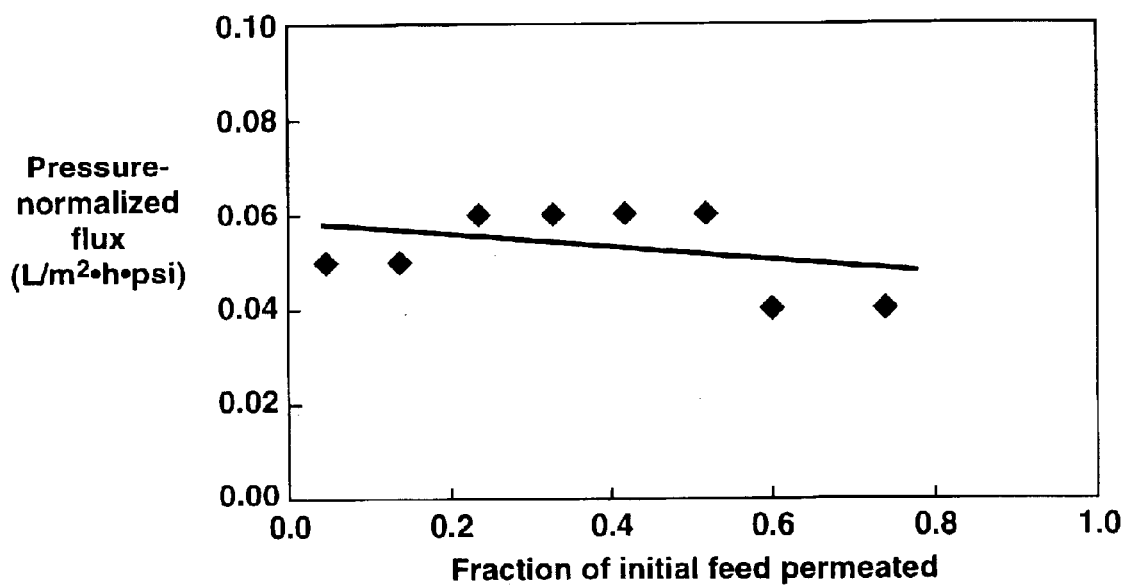
FIG. 15 shows the change in the pressure-normalized flux as a function of the fraction of feed permeated for the same experiment as FIGS. 13 and 14.

FIG. 15 shows the change in the pressure-normalized flux over the course of the experiment, expressed as a function of the fraction of the initial feed that had permeated the membrane when the measurement was taken. The pressure-normalized flux declined as the total solids concentration in the feed increased.

Example 14

Solution Volume Reduction of 90%

A concentration experiment similar to that of Example 13 was performed. Operating parameters were the same as in Example 13.

Figure 16:
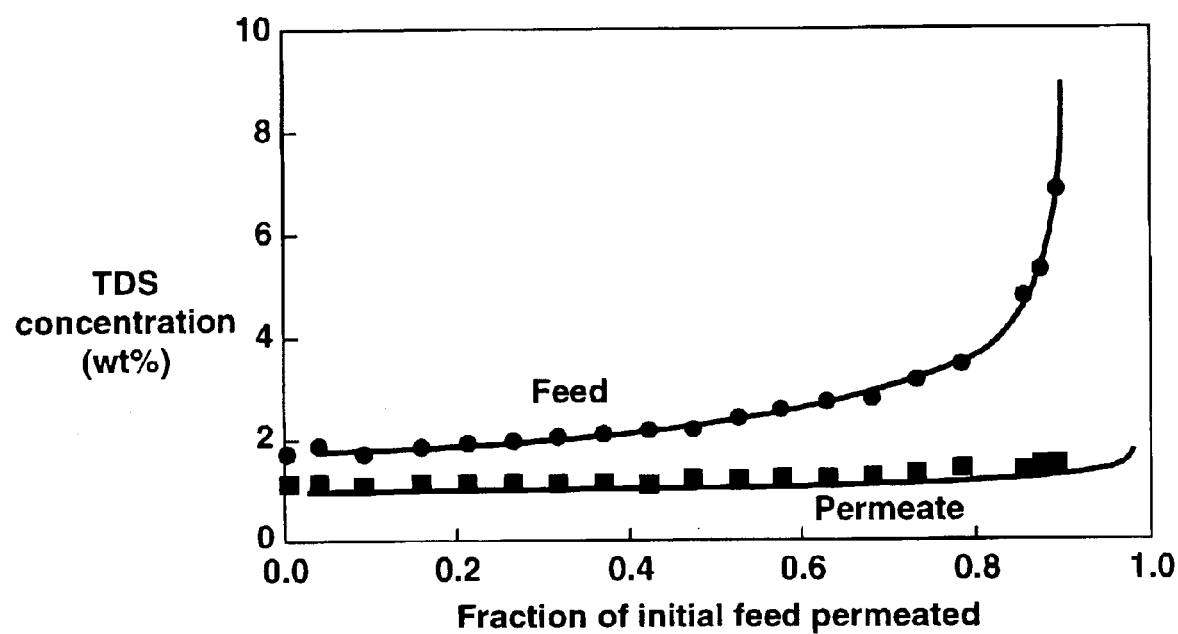
FIG. 16 shows the total dissolved solids concentrations in the feed and permeate for an experiment in which 90% reduction in solution volume was achieved. The figure also shows calculated concentration curves assuming 90% zein rejection and no sugar rejection by the membrane.

In this case, the goal of the experiment was to achieve 90% reduction in solution volume. At this point, the total dissolved solids content was found to have increased four-fold, from 1.7 wt % to 6.8 wt %, as shown in FIG. 16. The total dissolved solids concentration in the permeate remained low at about 1.0–1.5 wt %.

Figure 17:
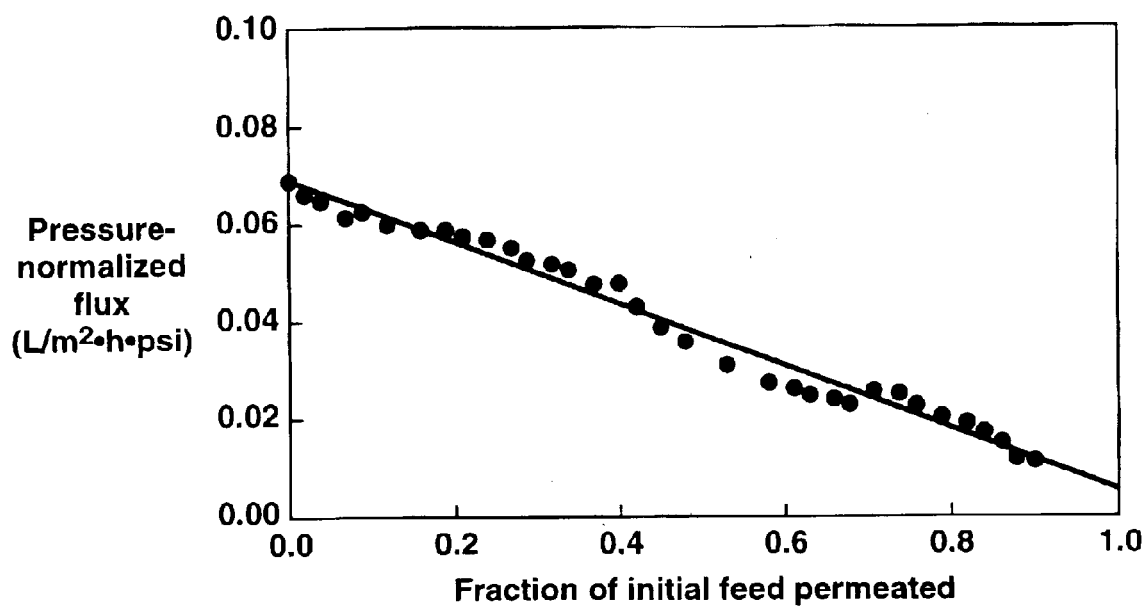
FIG. 17 is a graph showing the change in the pressure-normalized flux as a function of the fraction of feed permeated for the same experiment as FIG. 16.

FIG. 17 shows the change in the pressure-normalized flux over the course of the experiment. The pressure-normalized flux declined from about 0.07 $L/m^2 \cdot h \cdot psi$ to about 0.01 $L/m^2 \cdot h \cdot psi$ as the feed concentration increased.

Examples 15–17

Three-step Batch Diafiltration Experiment

Example 15

A concentration experiment was carried out using the same module and operating conditions as in Example 13 to concentrate a 120-L batch of feed solution in a solvent mixture of 70 vol % ethanol/30 vol % water containing an initial 1.36% wt % total dissolved solids.

The feed and permeate solutions were sampled from time to time and the total dissolved solids concentrations in the feed and permeate were measured.

Figure 18:
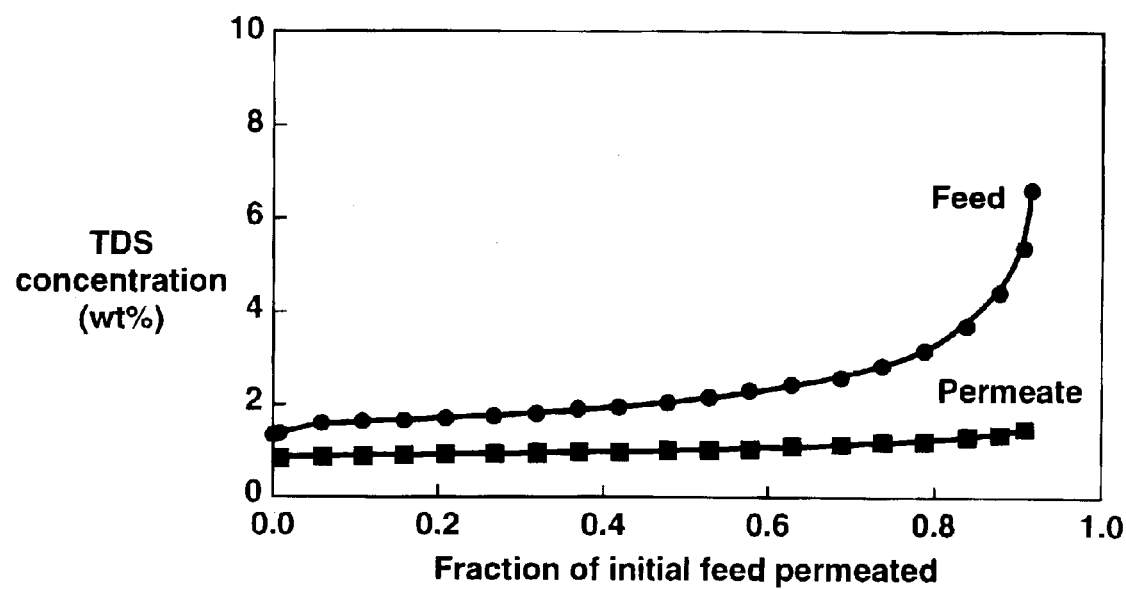
FIG. 18 is a graph showing the total dissolved solids concentrations in the feed and permeate for the first concentration step of a three-step batch diafiltration experiment.

FIG. 18 shows the experimental data points. The feed solution was concentrated from 1.36 wt % to 6.63 wt % total dissolved solids by permeating 92 vol % of the feed. The total solids concentration in the permeate remained low throughout the experiment, but increased slightly as the fraction of feed solution permeated went beyond 70–80%.

Feed and permeate samples were sent to the University of Illinois at Urbana-Champaign, where the zein concentration was determined by matrix-assisted laser desorption ionization mass spectroscopy (MALDI-MS). As the total solids concentration in the feed increased, the zein purity of the feed doubled from about 33% to about 67%.

The MALDI-MS analysis also showed that the overall zein rejection during the experiment was at least 99%, and that sugar rejection increased from 10% to 20% over the course of the experiment.

Figure 19:
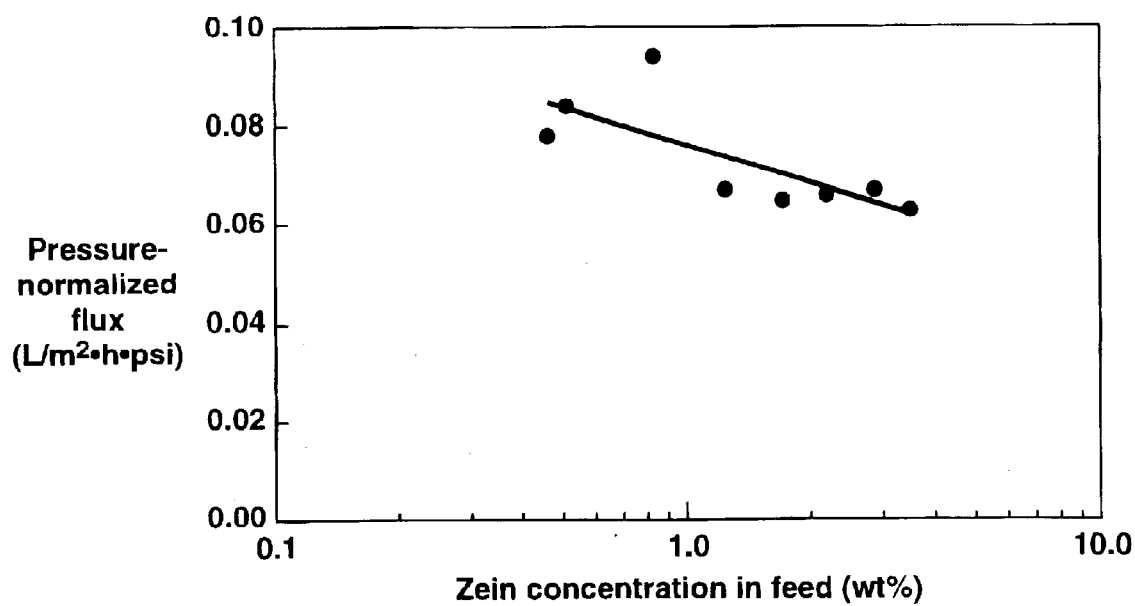
FIG. 19 is a graph showing the change in the pressure-normalized flux as a function of zein concentration in the feed for the same experiment as FIG. 18.

FIG. 19 shows the change in the pressure-normalized flux over the course of the experiment. From an initial value of 0.08 $L/m^2 \cdot h \cdot psi$, the pressure-normalized flux decreased to 0.06 $L/m^2 \cdot h \cdot psi$ by the end of the experiment.

Example 16

The concentrated extract obtained from the experiment of Example 15 was rediluted with the solvent mixture. Dilution reduced the total dissolved solids concentration of the extract from 6.6 wt % to 0.8 wt %.

Figure 20:
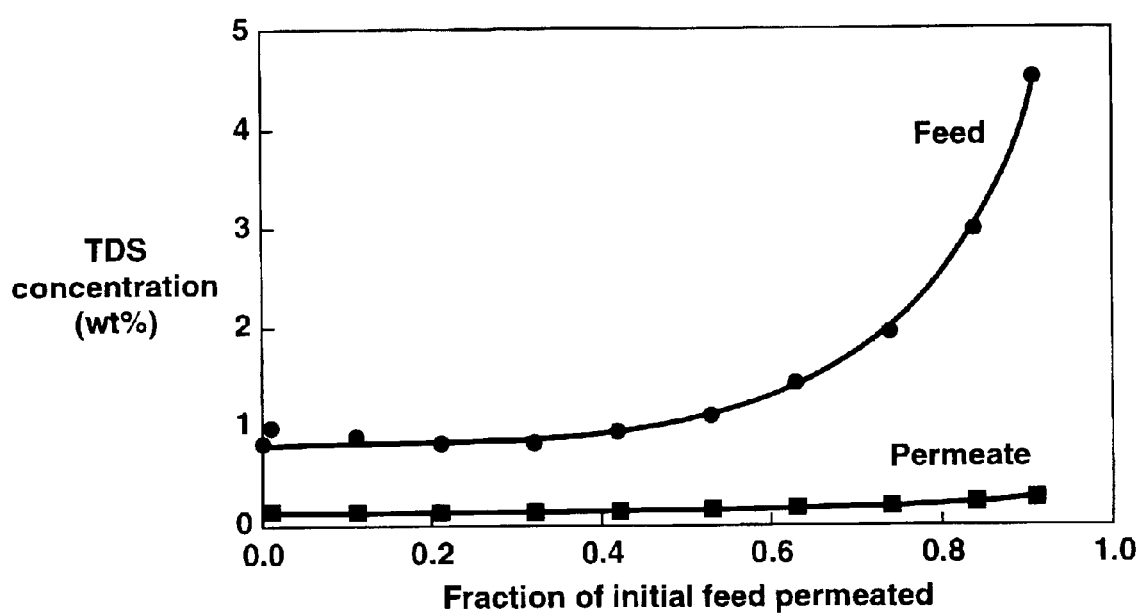
FIG. 20 is a graph showing the total dissolved solids concentrations in the feed and permeate for the second concentration step of a three-step batch diafiltration experiment.

The membrane concentration step was repeated as in Example 15. FIG. 20 shows that the total solids concentration in the feed was increased about five-fold, from 0.8 wt % to 4.5 wt % by permeating 91 vol % of the feed solution. The figure also shows that the total solids concentration in the permeate remains low, at less than 0.5 wt %.

Figure 21:
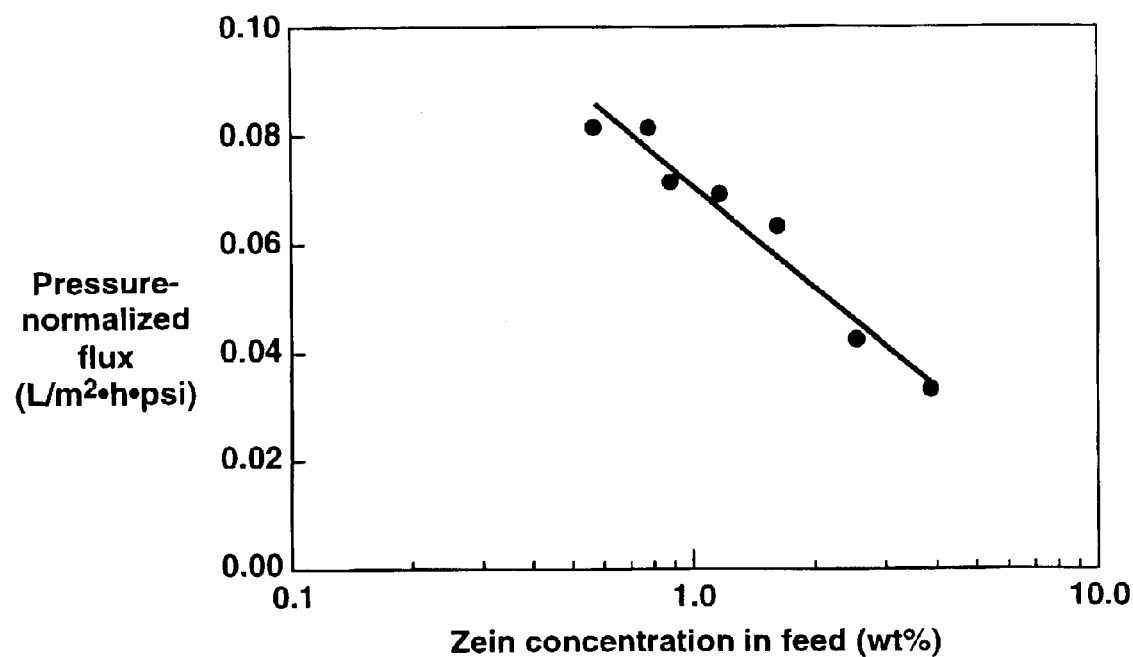
FIG. 21 shows the change in the pressure-normalized flux as a function of zein concentration in the feed for the same experiment as FIG. 20.

FIG. 21 shows the change in the pressure-normalized flux over the course of the experiment. The initial pressure-normalized flux was 0.08 $L/m^2 \cdot h \cdot psi$, the same as its original value at the start of the experiment of Example 15. The pressure-normalized flux declined to 0.03 $L/m^2 \cdot h \cdot psi$ by the end of the experiment.

Analysis as in Example 15 showed that the zein purity in the feed solids increased from 67% to 85%.

Example 17

The concentrated extract obtained from the experiment of Example 16 was rediluted with the solvent mixture, reducing the total dissolved solids concentration from 4.5 wt % to 0.8 wt %.

Figure 22:
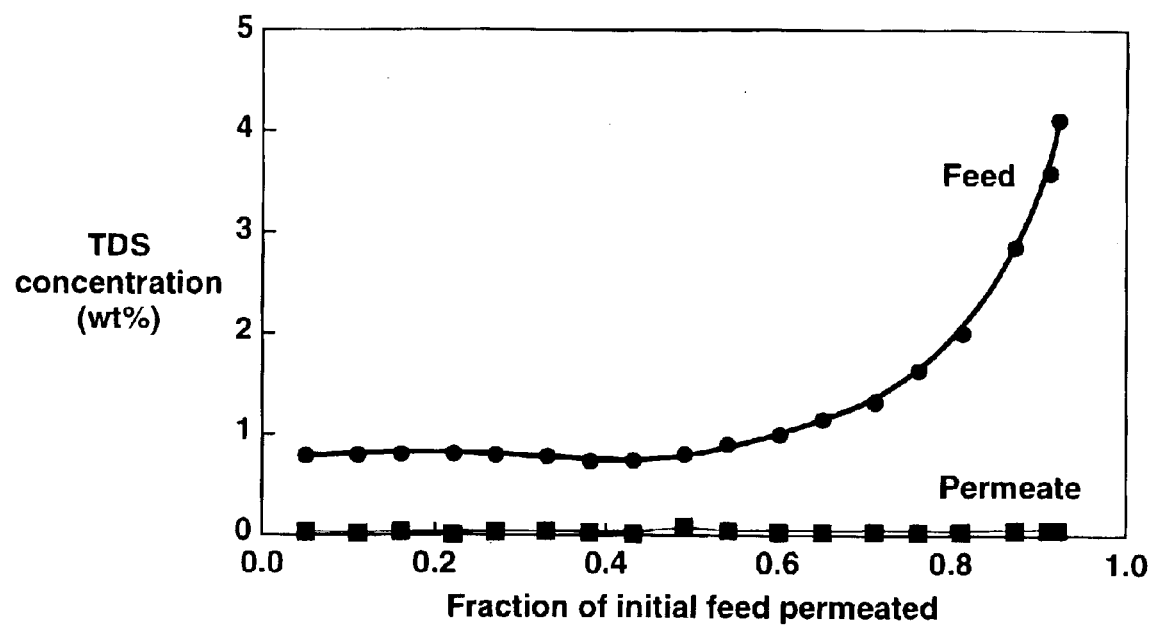
FIG. 22 is a graph showing the total dissolved solids concentrations in the feed and permeate for the third concentration step of a three-step batch diafiltration experiment.

The membrane concentration step was repeated as in Example 16. FIG. 22 shows that the total solids concentration in the feed was increased five-fold, from 0.8 wt % to 4.0 wt % by permeating 91 vol % of the feed solution. The figure also shows that the total solids concentration in the permeate remains very low, at less than 0.2 wt %.

Figure 23:
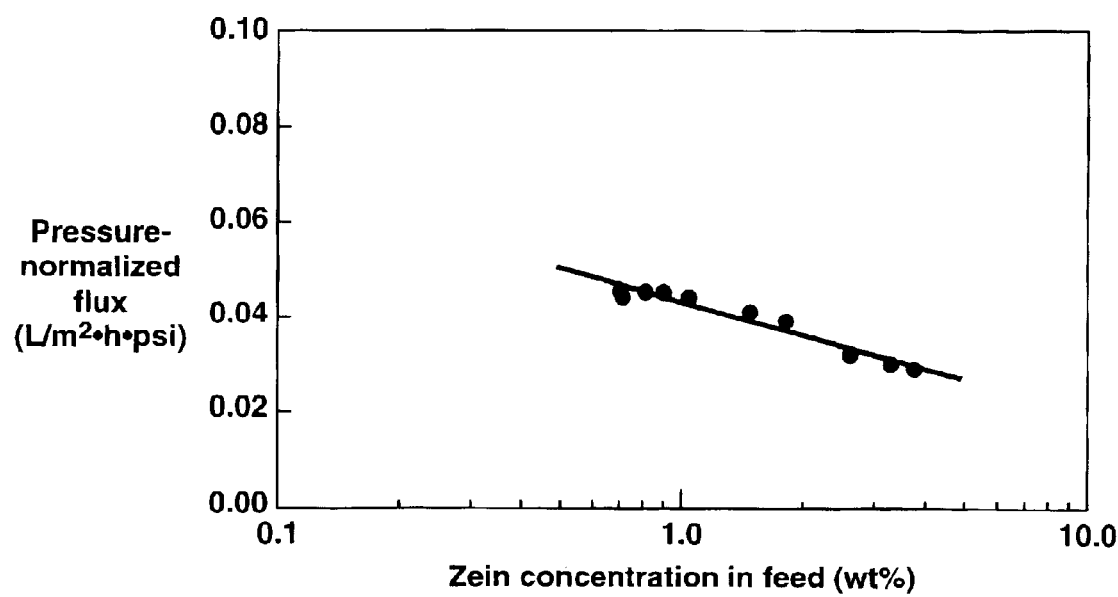
FIG. 23 shows the change in the pressure-normalized flux as a function of zein concentration in the feed for the same experiment as FIG. 22.

FIG. 23 shows the change in the pressure-normalized flux over the course of the experiment. The pressure-normalized flux declined from 0.05 $L/m^2 \cdot h \cdot psi$ to 0.03 $L/m^2 \cdot h \cdot psi$.

Figure 24:
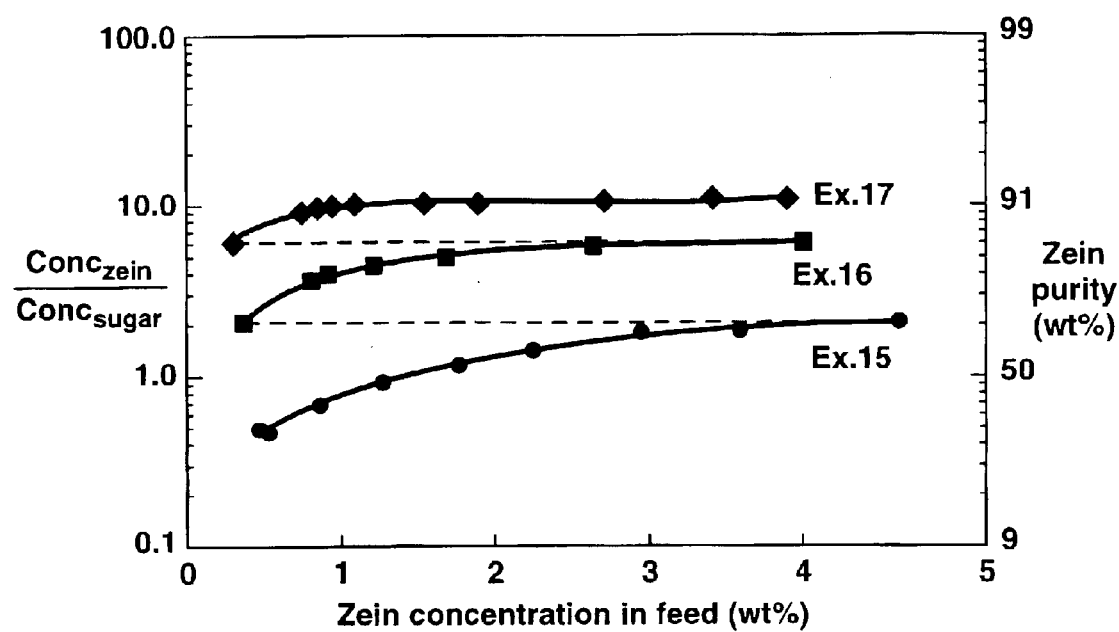
FIG. 24 shows the solids zein content, expressed as proportions of zein and sugar and percentage zein purity, as a function of the zein concentration in the feed solution for the three-step batch diafiltration experiment.

FIG. 24 shows the zein content of the total dissolved solids in the feed solution, expressed as concentration proportions of zein and sugar and percentage zein purity, as a function of the zein concentration in the feed solution for all three steps of the batch diafiltration experiments.

The first concentration step increased the zein purity from 33 wt % to 67 wt %, the second step from 67 wt % to 85 wt %, and the third step from 85 wt % to 92 wt %.

Example 18

A membrane module prepared as in Example 4 was used to carry out a series of flux experiments with feed solutions containing differing concentrations of dissolved solids. The solution was circulated through the module test system. Both residue and permeate streams were recirculated within the processing loop to maintain the same feed concentration throughout the experiment.

Solutions containing 0.8 wt %, 2 wt % and 4 wt % total dissolved solids in a 70 vol % ethanol/30 vol % water solvent were prepared. For each solution, a set of experiments at feed pressures varying from 50 psig to 150 psig was performed. The feed temperature was maintained at 25° C., and the feed solution flow rate was 3 gpm.

The goal of the experiments was to identify the optimum operating pressure range for each solution, that is the range in which flux has not yet become independent of applied pressure.

Figure 25:
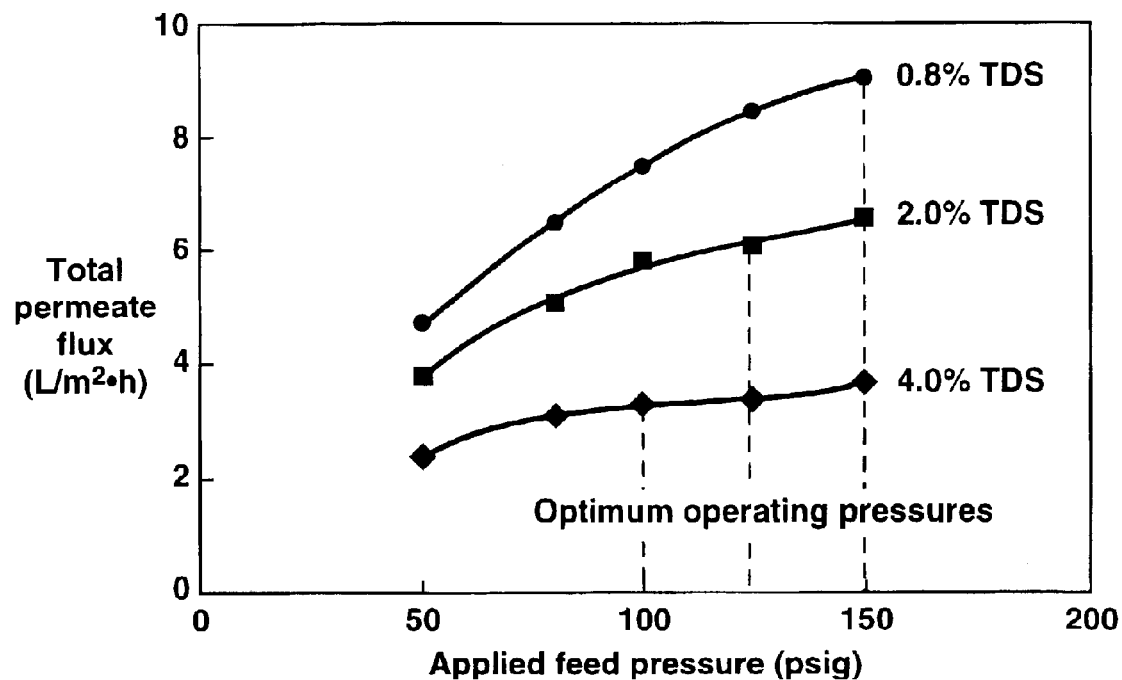
FIG. 25 is a graph of total permeate flux as a function of applied feed pressure for feed solutions of differing solids concentrations.

The results of the experiments are summarized in FIG. 25. As expected, both feed concentration and feed pressure are factors that affect transmembrane flux. Flux is inversely dependent on feed concentration. The higher the feed concentration, the more likely is a concentration polarization gel layer to form on the membrane surface, and the thicker and more viscous is that gel likely to be.

Also as expected, flux initially increases linearly with increase in feed pressure. At higher feed pressure, flux gradually levels off, consistent with a progressively increasing resistance to permeation created by the gel layer on the membrane surface.

The dashed lines in FIG. 25 indicate roughly the maximum preferred operating pressure for each feed to keep the process in the pressure-dependent region. For the 0.8 wt % solution, flux was still increasing with increasing pressure up to 150 psig. For the 2 wt % solution, flux had leveled off substantially by a feed pressure of about 120 psig, and for the 4 wt % solution by about 100 psig.

We claim:

1. A process for treating a zein solution comprising zein and a solvent, comprising the steps of;
   (a) providing a first composite membrane having a first feed side, a fist permeate side, and a first dense, non-porous selective layer that is selective in favor of the solvent over zein;
   (b) passing the zein solution across the first feed side;
   (c) withdrawing from the first feed side a fist residue stream enriched in zein compared to the zein solution;
   (d) withdrawing from the first permeate side a first permeate stream depleted in zein compared to the zein solution.

2. The process of claim 1, wherein the first dense, non-porous selective layer is hydrophilic.

3. The process of claim 1, wherein the first dense, non-porous selective layer comprises a polymer including a polyether segment.

4. The process of claim 1, wherein the first dense, non-porous selective layer comprises a polymer including a polyether segment and a hydrophilic segment.

5. The process of claim 1, wherein the first dense, non-porous selective layer comprises a polyamide-polyether block copolymer.

6. The process of claim 1, wherein the first composite membrane comprises a support layer for supporting the first dense, non-porous selective layer and a top layer coated on the first dense, non-porous selective layer.

7. The process of claim 1, wherein the solvent is non-aqueous based.

8. The process of claim 1, wherein the solvent comprises an alcohol.

9. The process of claim 1, wherein the solvent comprises ethanol.

10. The process of claim 1, wherein the solvent comprises an ethanol/water mixture.

11. The process of claim 1, operated under an applied feed pressure of no higher than about 150 psig.

12. The process of claim 1, operated under an applied feed pressure between about 50 psig and 150 psig.

13. The process of claim 1, operated in a feed-and-bleed mode by recirculating a portion of the first residue stream and adding it to the zein solutions.

14. The process of claim 1, operated in a diafiltration mode by diluting and further processing at least a portion of the first residue steam.

15. The process of claim 14, wherein a diluent is used for the diluting step, and the diluent has a different composition than the solvent.

16. The process of claim 1, wherein the first composite membrane exhibits a zein rejection, averaged over the duration of the process, of at least about 80%.

17. The process of claim 1, wherein the first composite membrane exhibits a zein rejection, averaged over the duration of the process, of at least about 90%.

18. The process of claim 1, wherein the zein solution further comprises at least one sugar and the first composite membrane exhibits a total sugars rejection, averaged over the duration of the process, of no more than about 40%.

19. The process of claim 1, wherein the first composite membrane exhibits a pressure-normalized permeate flux, averaged over the duration of the process, of at least about 0.05 L/m²·h·psi.

20. The process of claim 1, wherein the first residue stream has a residue volume flow and the zein solution has a feed volume flow and the residue volume flow is no more than about 30 vol % of the feed volume flow.

21. The process of claim 1, wherein the first residue stream has a residue volume flow and the zein solution has a feed volume flow and the residue volume flow is no more than about 20 vol % of the feed volume flow.

22. The process of claim 1, wherein the zein solution has a first zein concentration and the first residue stream has a second zein concentration that is between about five and 10 times greater than the first zein concentration.

23. The process of claim 1, wherein the first residue stream has a total dissolved solids content and a zein content, and wherein the zein content is at least about 70% of the total dissolved solids content.

24. The process of claim 1, wherein the first residue stream has a total dissolved solids content and a zein content, and wherein the zein content is at least about 80% of the total dissolved solids content.

25. The process of claim 1, wherein the first composite membrane has a molecular weight cut-off above about 2,000 dalton and below about 12,000 dalton.

26. The process of claim 1, wherein the first composite membrane has a molecular weight cut-off above about 12,000 dalton and below about 22,000 dalton.

27. The process of claim 1, wherein the first residue stream is subjected to further treatment.

28. The process of claim 27, wherein the further treatment comprises at least one additional membrane treatment using at least one additional composite membrane having a dense, non-porous selective layer.

29. The process of claim 1, further comprising the steps of:
   (e) providing a second composite membrane having a second feed side, a second permeate side, and a second dense, non-porous selective layer that is selective in favor of the solvent over zein;
   (f) passing at least a portion of the first residue steam across the second feed side;
   (g) withdrawing from the second feed side a second residue stream enriched in zein compare to the first residue stream;
   (h) withdrawing from the second permeate side a second permeate stream depleted in zein compared to the first residue stream.

30. The process of claim 29, wherein step (b) is operated under a first applied pressure and step (f) is operated under a second applied pressure and wherein the second applied pressure is lower than the first applied pressure.

31. The process of claim 1, wherein the first residue stream is spray dried to produce zein powder.

32. The process of claim 1, wherein the first residue stream is subjected to evaporation followed by spray drying to produce zein powder.

33. The process of claim 1, wherein the first permeate stream is subjected to further treatment.

34. The process of claim 1, further comprising warming the zein solution prior to step (b).

35. The process of claim 1, further comprising warming the zein solution to a temperate up to about 35° C. prior to step (b).

36. A process for treating a feed solution comprising a solvent and a solute, the solute comprising zein and a sugar, comprising the steps of:

(a) providing a first composite membrane having a first feed side, a first permeate side, and a first dense, non-porous selective layer that is selective in favor of the solvent over zein and that exhibits a zein rejection and a sugar rejection, the sugar rejection being lower than the zein rejection;

(b) passing the feed solution across the first feed side;

(c) withdrawing from the first feed side a first residue stream enriched in zein compared to the feed solution;

(d) withdrawing from the first permeate side a first permeate stream having a permeate dissolved solids content that is enriched in sugar and depleted in zein compared to the solute.

37. The process of claim 36, wherein the first dense, non-porous selective layer comprises a polyamide-polyether block copolymer.

38. The process of claim 36, wherein the solvent comprises ethanol.

39. The process of claim 36, operated in a diafiltration mode by diluting and further processing at least a portion of the first residue stream.

40. The process of claim 36, wherein the zein rejection, averaged over the duration of the process, is at least about 90%.

41. The process of claim 36, wherein the sugar rejection, averaged over the duration of the process, is no more than about 40%.

42. The process of claim 36, wherein the first composite membrane exhibits a pressure-normalized permeate flux, averaged over the duration of the process, of at least about 0.05 L/m$^2$·h·psi.

43. The process of claim 36, wherein the first residue stream has a residue volume flow and the feed solution has a feed volume flow and the residue volume flow is no more than about 30 vol % of the feed volume flow.

44. The process of claim 36, wherein the first composite membrane has a molecular weight cut-off above about 2,000 dalton and below about 12,000 dalton.

45. The process of claim 36, wherein the first residue stream is subjected to at least one additional membrane treatment using at least one additional composite membrane having a dense, non-porous selective layer.

46. The process of claim 36, wherein at least a portion of the first residue stream is spray dried to produce zein powder.

47. A process for treating a zein solution comprising zein and a non-aqueous based solvent, comprising the steps of:

(a) providing a first composite membrane having a first feed side, a first permeate side, and a first dense, non-porous selective layer that is selective in favor of the solvent over zein;

(b) passing the zein solution across the first feed side;

(c) withdrawing from the first feed side a first residue stream enriched in zein compared to the zein solution;

(d) withdrawing from the first permeate side a first permeate steam-depleted in zein compared to the zein solution.

48. The process of claim 47, wherein the first dense, non-porous selective layer comprises a polymide-polyether block copolymer.

49. The process of claim 47, wherein the solvent comprises ethanol.

50. The process of claim 47, operated in a diafiltration mode by diluting and further processing at least a portion of the first residue stream.

51. The process of claim 47, wherein the first composite membrane exhibits a zein rejection, averaged over the duration of the process, of at least about 90%.

52. The process of claim 47, wherein the zein solution further comprises at least one sugar and the first composite membrane exhibits a total sugars rejection, averaged over the duration of the process, of no more than about 40%.

53. The process of claim 47, wherein the first composite membrane exhibits a pressure-normalized permeate flux, averaged over the duration of the process, of at least about 0.05 L/m$^2$·h·psi.

54. The process of claim 47, wherein the first residue stream has a residue volume flow and the zein solution has a feed volume flow and the residue volume flow is no more than about 30 vol % of the feed volume flow.

55. The process of claim 47, wherein the first composite membrane has a molecular weight cut-off above about 2,000 dalton and below about 12,000 dalton.

56. The process of claim 47, wherein the first residue stream is subjected to at least one additional membrane treatment using at least one additional composite membrane having a dense, non-porous selective layer.

57. The process of claim 47, wherein at least a portion of the first residue stream is spray dried to produce zein powder.

* * * * *